US006451528B1

(12) United States Patent
Carr et al.

(10) Patent No.: US 6,451,528 B1
(45) Date of Patent: Sep. 17, 2002

(54) SPERM-SPECIFIC AKAP PROTEIN GENES AND USES

(75) Inventors: Daniel W. Carr, Portland, OR (US); Srinivasan Vijayaraghavan, Kent, OH (US)

(73) Assignee: Oregon Health & Sciences University, Portland, OR (US)

( * ) Notice: Subject to any disclaimer, the term of this patent is extended or adjusted under 35 U.S.C. 154(b) by 0 days.

(21) Appl. No.: 09/268,480

(22) Filed: Mar. 16, 1999

(51) Int. Cl.[7] ................................................. C12Q 1/68
(52) U.S. Cl. ..................... 435/6; 435/320.1; 435/252.3; 435/254.11; 435/325; 435/419; 536/23.1; 536/23.2
(58) Field of Search ............................... 536/23.1, 23.2, 536/24.31, 24.5; 435/320.1, 252.3, 254.11, 419, 325, 6

(56) References Cited

PUBLICATIONS

Feliciello et al. Expression of A Kinase Anchor Protein 121 is Regulated by Hormones in Thyroid and Testicular Germ Cells. J. of Biol. Chemistry (1998) 273(36):23361–23366, Sep. 1998.*
GenBank Accession No. AF087003 (1998), Sep. 1998.*
GenBank Accession No. AF093408 (1998), Oct. 1998.*
GenBank Accession No. AF093407 (1998), Oct. 1998.*
GenBank Accession No. AF093406 (1998), Oct. 1998.*
Maniatis et al. Molecular Cloning: A Laboratory Manual (1982) Cold Spring Harbor Press, pp. 404–433.*
Carrera et al. Regulation of Protein Tyrosine Phosphorylation in Human Sperm by Calcium/Calmodulin–Dependent Mechanism: Identification of A Kinase Anchor Proteins as Major Substrates for Tyrosine Phosphorylation. Developmental Biology (1996) 180: 284–2, Nov. 1996.*
Tash, 1989, Cell Motil. Cytoskel. 14: 332–339.
Bedford and Hoskins 1990, in Marshall's Physiology of Reproduction, (Lamming, ed.), Churchill Livingstone: New York, p. 379: Chapter 5.
Hoskins et al., 1974, J. Reprod. Fertil. 37: 131–133.
Garbers et al., 1972 Biol. Reprod. 7: 132 (Abstract).
Garbers et al., 1978, Adv. Cyclic Nucleotide Res. 9:583–595.

(List continued on next page.)

*Primary Examiner*—Tekchand Saidha
*Assistant Examiner*—Kathleen Kerr
(74) *Attorney, Agent, or Firm*—McDonnell Boehnen Hulbert & Berghoff

(57) ABSTRACT

This invention provides isolated nucleic acid encoding sperm-specific protein kinase A anchoring proteins from mammalian species, recombinant expression constructs encoding said mammalian sperm-specific protein kinase A anchoring proteins, cells transformed with said constructs, and homogenous preparations of these proteins prepared using recombinant genetic techniques. The invention also provides analytic tools such as polyclonal antisera and monoclonal antibodies specific for said sperm-specific protein kinase A anchoring proteins of the invention. The invention also provides methods for isolating nucleic acid encoding mammalian sperm-specific protein kinase A anchoring proteins and recombinant genetic methods for producing said mammalian sperm-specific protein kinase A anchoring proteins of the invention. The invention particularly provides high throughput screening methods for screening compounds that can disrupt binding between protein kinase A and the sperm-specific protein kinase A anchoring protein and methods for determining and producing compounds, particularly antisense oligonucleotides, for inhibiting or preventing expression of sperm-specific protein kinase A anchoring protein in sperm, spermatids, or progenitor cells thereof. These methods are useful for development of effective, male-specific contraceptives, which are also provided by the invention.

21 Claims, 14 Drawing Sheets

OTHER PUBLICATIONS

Garbers and Kopf, 1980, in Advances in Cyclic Nucleotide Research, (Greengard and Robinson, eds.), vol 13, Raven Press: New York, pp. 252–306.
Lindemann and Kanous, 1989, Arch. Androl. 23: 1–22.
Tash & Means, 1988, Prog. Clin. Biol. Res. 267: 335–355.
Carr et al., 1991., J. Biol. Chem. 266: 14188–14192.
Rubin, 1994 Biochem. Biophys. Acta 1224: 467–479.
Dell' Acqua & Scott, 1997, J. Biol. Chem. 272:12881–4.
Faux et al., 1996, Cell 85: 9–12.
Pawson et al., 1997, Science 278: 2075–2080.
Carr et al., 1992, J. Biol. Chem. 267: 13376–13382.
Huang et al., 1997, Proc. Acad. Sci. USA 94:11184–11189.
Friend, 1982, J. Cell Biol. 93:243–249.
Vijayaraghaven et al. 1985, Biol. Reproduc. 32: 489–500.
Mohapatra et al., 1998, Biochem, Biophys. Res. Commun. 244: 540–545.
Vijayaraghaven et al., 1997, J. Biol. Chem. 272: 4747–4752.
Johnson et al., 1997, Devel. Biol. 192: 340–350.
Visconti et al., 1997, Devel. Biol. 192: 351–363.
Sanger et al., 1997, Proc. Natl. Acad. Sci. USA 74:5463–5467.
Kozak, 1987, Nucleic Acids Res. 15:8125–8148.
Bairoch et al., 1997, Nucleic Acids. Res. 25:217–221.
Hirokawa et al., 1998, Bioinformatics 14:378–379.
Altschult et al., 1990, J. Molec. Biol. 215:403–410.
Carrera et al., 1994, Develop. Biol. 165:272–284.
Fulcher et al., 1995, Biol. Reprod. 52: 41–49.

* cited by examiner

FIG. 2A

| | | | | | | | |
|---|---|---|---|---|---|---|---|
| Human | MSEKVDWLQSQNGVCKVDVYSPGDNQ | AQDWKMDT | – – – – – – – – – – – | STDPVRVLSWLRRDLEKSTAE |
| Murine | MADRVDWLQSQSGVCKVDVYSPGDNQH | QDWKMDT | – – – – – – – – – – – | STDPVRVLSWLRRDLEKSTAG |
| Bovine | VDWLQSQNGVCKVDVYSPGDSQP | QDWKMS | DESLSIFKEASHDPIR | VLSWLRRDLEKSTAG |

| Human | FQDVRFKPGES – FGGETSNSGDPHKG | FSVDYYNTTTKG | TPERLHFEMTHKEIPCQGPRAQLGNG |
| Murine | FQDSRFKPGESSFVEEVAYPVDQRKG | FCVDYYNTTNKGSPGRLHFEMSHKENPSQGLISHVGNG |
| Bovine | FQDIRFKPGESSLGREMVSGDPRKG | FCVDYYNTTSRGSPGRLHFEMSHRENPHQGP – – TCNG |

| Human | SSVDEVSFYANRLTNLVIAMARKEINEKIDGSENKCVYQSLYMGNEPTPTKSLSKIASELVNET |
| Murine | GSIDEVSFYANRLTNLVIAMARKEINEKIHGAENKCVHQSLYMGDEPTPHKSLSTVASELVNET |
| Bovine | SSVDEVSFYANRLTNLVIAMARKEINEKIDGSENRCVHQSVYMGDEPPPNKSLSKVASELVNET |

| Human | VSACSRNAAPDKAPGSGDRVSGSQSPPNLKYKSTLKIKESTKERQGPDDKPPSKKSFFYKEVF |
| Murine | VTACSKNISDKAPGSGDRASGSQ – APGLRYMSTLKIKESTKEGKCPDDKPFKKSFFYKEVF |
| Bovine | VTACSKNTPSDKAPGSGDRASGTLQSPPNLKYKSTLKIKESNKGRGPDDRPSKKSLFYKEVF |

| Human | ESRNGDYAREGGRFFPRERKRFRGQE – RPDDFTASVSEGIMTYANSVVSDMMVSIMKTLKIQV |
| Murine | ESRNAGDAKEGGRSLPGDQKLFRTSPDNRPDDFSNSISQGIMTYANSVVSDMMVSIMKTLKIQV |
| Bovine | ESRNAGDAKEGGRTLPAERKMFRGYE – RPDDFTASISQGIMTYANSVVSDMMVSIMKTLKIQV |

| Human | KDTTIATILLKKVLLKHHAKEVVSDLIDSFLRNLHSVTGTLMTDTQFVSAVKRTVFSHGSQKATD |
| Murine | KDTTIATILLKKVLMKHAKEVVSDLIDSFMKNLHGVTGSLMTDTDFVSAVKRSFFSHGSQKATD |
| Bovine | KDTTIATIVLKKVLIKHAKEVVSDLIDSFMKNLHNVTGTLMTDTDFVSAVKRSFFSHGSQKATD |

| Human | IMDAMLRKLYNVMFAKKVPEHVRKAQDKAESYSLISMKGMG – DPKNRNVNFAMK – SETKLREKM |
| Murine | IMDAMLGKLYNVMFAKKFPENIRARDKSESYSLIISMKGMGSRAGDPKLSNLNFAMK – SESKLKENL |
| Bovine | IMDAMLGKLYSVIFAKKPETVRKTKDKSESYSLVSMKGMG – DPKHRNVNFASMKEGKVRERV |

FIG. 2B

[Sequence alignment figure comparing Human, Murine, and Bovine protein sequences across multiple aligned blocks]

RII Overlay                         Western

FIG. 5A

RII Binding Domains

| | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| AKAP110 (124-141) | E | V | S | F | Y | A | N | R | L | T | N | L | V | I | A | M | A | R |
| AKAP82 (207-224) | D | L | S | F | Y | V | N | R | L | S | S | L | V | I | Q | M | A | R |
| S-AKAP84 (343-360) | E | I | K | R | A | A | F | Q | I | S | Q | V | I | S | E | A | T |   |
| TAKAP80 (342-359) | R | M | N | E | I | A | R | T | V | E | G | L | V | T | A | A | S | V |
| MAP2 (86-103) | T | A | E | E | V | S | A | R | I | V | Q | V | V | T | A | E | A | V |
| Ht31 (494-511) | L | I | E | E | A | A | S | R | I | V | D | A | V | I | E | Q | V | K |
| AKAP150 (428-445) | L | L | I | E | T | A | S | S | L | V | K | N | A | I | Q | L | S | V |
| AKAP79 (391-408) | L | L | I | E | T | A | A | S | L | V | K | N | A | I | Q | L | S | I |
| AKAP95 (565-582) | T | P | E | E | K | V | A | E | V | L | A | E | V | I | T | A | A | V |
| AKAP120 (499-516) | L | E | E | K | Q | Y | A | R | K | V | L | V | A | L | A | E | A | V |
| AKAP220 (794-811) | T | E | E | T | K | S | S | K | L | V | Q | D | L | I | Q | T | A | V |
| Gravin (1443-1460) | E | L | E | Y | Q | A | G | L | L | V | Q | N | A | I | E | L | S | L |
| AKAP-KL (585-602) | P | L | E | Y | R | L | S | K | R | L | V | E | N | A | V | L | K | A |
| AKAP18 (28-45) | E | L | V | R | L | S | K | R | L | V | E | N | A | V | L | K | A | I |
| Ezrin (413-430) | S | Q | E | Q | L | A | A | E | L | A | E | Y | T | A | K | I | A | L |

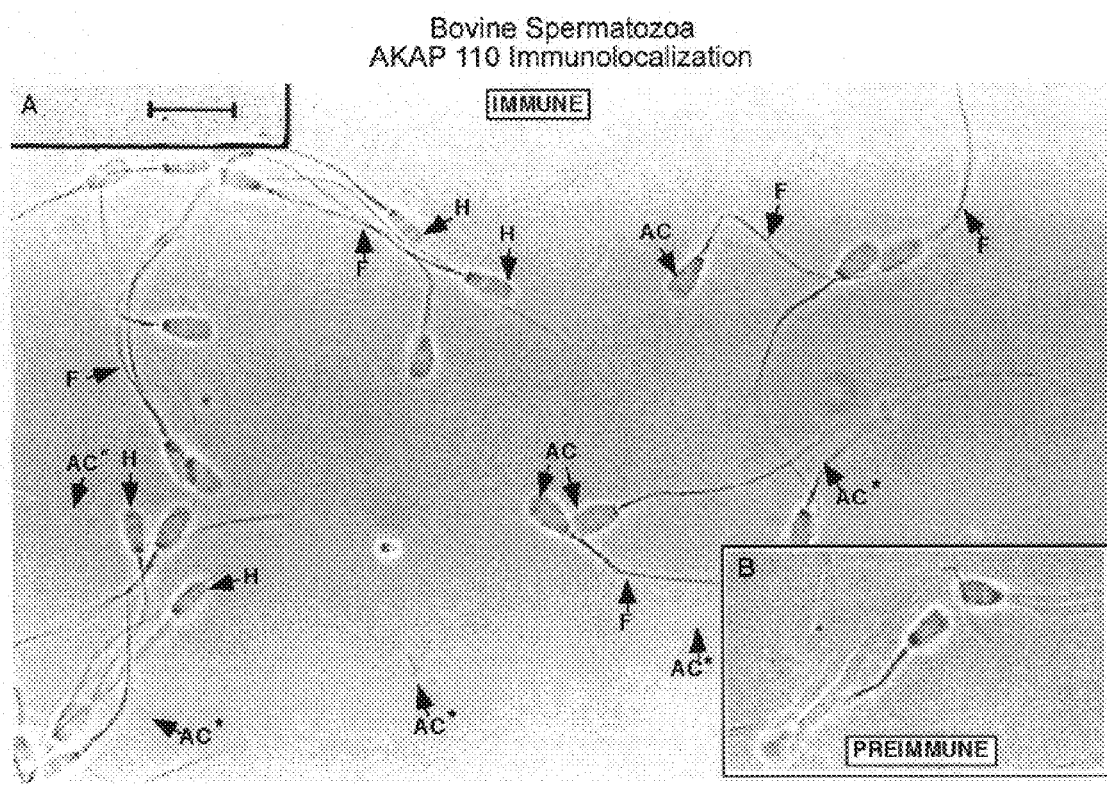

Bovine Spermatozoa
AKAP 110 Immunolocalization

SPERM-SPECIFIC AKAP PROTEIN GENES AND USES

This invention was made with government support under grant number R29HD32508 from the National Institutes of Health. The government has certain rights in the invention.

BACKGROUND OF THE INVENTION

1. Field of the Invention

This invention relates to sperm-specific protein kinase A anchoring proteins from mammalian species and the genes encoding such proteins. Specifically, the invention relates to the isolation of nucleic acid encoding sperm-specific protein kinase A anchoring proteins from mammalian species, and the production of homogenous preparations of such proteins using recombinant genetic techniques. The invention also relates to the preparation of analytic tools such as polyclonal antisera and monoclonal antibodies specific for said sperm-specific protein kinase A anchoring proteins. Importantly, the invention is related to high throughput screening of compounds that can disrupt binding between protein kinase A and the sperm-specific protein kinase A anchoring proteins of the invention, or that inhibit or prevent expression of the sperm-specific protein kinase A anchoring proteins in sperm, spermatids or progenitor cells thereof, for development of effective contraceptives, and provides antisense oligonucleotides, agents and compounds detected using the screening methods of the invention as reversible, male contraceptive agents.

2. Background of the Invention

Signal transduction enzymes such as protein kinases and phosphatases play pivotal roles in mediating cellular responses to a wide variety of stimuli. Cyclic AMP (cAMP) mediates the motility of sperm and a variety of other ciliated cells (Satir, 1985, *Molec. Cell Biol.* 4: 1–46n Tash, 1989, *Cell Motil. Cytoskel.* 14: 332–339; Bedford and Hoskins 1990, in MARSHALL'S PHYSIOLOGY OF REPRODUCTION, (Lamming, ed.), Churchill Livingstone: New York, p.t379). Increases in the level of this nucleotide are associated with development of sperm motility in the epididymis (Bedford and Hoskins, ibid.; Hoskins et al., 1974, *J. Reprod. Fertil.* 537: 131–133). Cell-permeant cAMP analogs, cAMP phosphodiesterase inhibitors, and adenylyl cyclase activators all stimulate motility of sperm from several species (Garbers et al., 1972, *Biol. Reprod.* 7: 132; Garbers et al., 1978, *Adv. Cyclic Nucleotide Res.* 9: 583–595). Flagellar activity in sperm has been shown to be regulated by cAMP (Tash, ibid.; Garbers and Kopf, 1980, in ADVANCES IN CYCLIC NUCLEOTIDE RESEARCH, (Greengard and Robison, eds.), Vol. 13, Raven Press: New York, pp. 252–306; Lindemann and Kanous, 1989, *Arch. Androl.* 23: 1–22; Tash & Means, 1–988, *Prog. Clin. Biol. Res.* 267: 335–355).

The cAMP-dependent protein kinase (PKA) is a ubiquitous, multifunctional enzyme involved in the regulation of a diverse array of cellular events. PKA holoenzyme consists of four subunits, two catalytic (C) and two regulatory (R). In the absence of cAMP, the regulatory subunits keep the catalytic subunits inactive. Cyclic AMP binding to the regulatory subunit promotes dissociation from and activation of the catalytic subunits. There are two R subunit classes, RI and RII, which form the type I and type II holoenzymes, respectively. Type II PKA is present in all cells, whereas the tissue distribution of type I PKA is more restricted. Subcellular localization of PKA is directed through the regulatory (R) subunit. Recent studies have shown that PKA is anchored at specific subcellular sites through the interaction of its regulatory subunit with A-kinase anchoring proteins (AKAPs) (Carr et al., 1991, *J. Biol. Chem.* 266: 14188–14192; Rubin, 1994, *Biochim. Biophys.* Acta 1224: 467–479; Dell'Aqua & Scott, 1997, *J. Biol. Chem.* 272: 12881–4; Faux et al., 1996, *Cell* 85: 9–12; Pawson et al., 1997, *Science* 278: 2075–2080).

A number of AKAPs have been cloned and biochemically characterized (Dell'Aqua & Scott, ibid.). All AKAPs contain a common structural motif that binds with nanomolar (nM) affinity to the regulatory subunit of PKA (Carr et al., 1991, ibid.; Carr et al., 1992, *J. Biol. Chem.* 267: 13376–13382). Certain of the anchoring proteins that are capable of binding both RI and RII have been labeled dual (D)-AKAPs (Huang et al., 1997, *J. Biol. Chem.* 272: 8057–8064; Huang et al., 1997, *Proc. Natl. Acad. Sci.* USA 94: 11184–11189). Since PKA has broad substrate specificity, presumably one of the primary functions of PKA anchoring is to spatially restrict its action, thus providing specificity of function.

Because cAMP analogs and agents that increase intracellular cAMP are potent stimulators of sperm motility, the role of PKA and AKAP subcellular localization of PKA was expected by the inventors to be important for understanding and modulating sperm motility. The highly polarized sperm cell is particularly well suited for investigating the structure and function of PKA anchoring proteins. Differentiated sperm have a number of district subcellular structures. The microtubular apparatus in mammalian sperm is surrounded by district cellular organelles such as the outer dense fibers and fibrous sheath. The cytoplasmic volume of the sperm cell is considerably lower than that of most somatic cells. Free diffusion of plasma membrane proteins is apparently restricted to three distinct domains, defined by the sperm head, midpiece and tail regions (Friend, 1982, *J. Cell Biol.* 93: 243–249). This unique compartmentalization of the sperm cell made it an excellent model system to study the role of targeting and anchoring of PKA and other enzymes in regulating cell function.

Regulation of sperm motility also provides an important avenue for developing a new generation of contraceptive agents. In the past, contraception has relied on barrier methods (such as condoms) and in regulating a female's capacity to be impregnated or the fertilized zygote to attach to the uterus (examples include the intrauterine device and "the Pill"). Regulation of cAMP-stimulated sperm motility by targeting the PKA/AKAP interaction provides for the first time a male-specific route of contraceptive intervention.

There thus remains a need in this art for specific, effective, reversible, reliable male contraceptive with minimal physiological or systemic side effects. As disclosed herein, one particular PKA anchoring protein, termed AKAP110, is uniquely expressed in sperm, making it possible that therapies which interfere with or prevent expression of this protein could be used as a contraceptive. One example of such an approach is to use antisense oligonucleotides to inhibit or prevent AKAP110 gene expression in developing sperm or spermatids, which have been shown to express this protein. Antisense-based therapeutics are already being used in humans, and it is likely that systemic administration of antisense reagents will be achieved in the near future. Antisense approaches to male contraception have clear advantages over other methods, such as hormonal or immunological methods, such as being completely reversible and in having a likelihood of fewer and less physiologically significant side effects. Other examples of novel contraceptive approaches is the use of peptides or small molecules that directly interfere with the AKAP110: PKA binding interaction in the absence of threshold levels of cAMP.

SUMMARY OF THE INVENTION

The present invention relates to the cloning, expression and functional characterization of mammalian sperm-specific protein kinase A anchoring protein having an apparent molecular weight of about 110 kildaltons, termed "AKAP110" herein.

This invention specifically provides isolated nucleic acid encoding sperm-specific protein kinase A anchoring protein from human, bovine and murine male germ cells, recombinant expression constructs comprising said nucleic acid, and cells transformed with such recombinant expression constructs and producing the sperm-specific protein kinase A anchoring protein thereby. The invention also provides homogenous preparations of sperm-specific protein kinase is A anchoring protein, and antibodies raised against and that immunologically recognize said protein. The invention also provides methods for producing said homogeneous preparation of the sperm-specific protein kinase A anchoring proteins of the invention using said cells transformed with the recombinant expression constructs of the invention. The invention advantageously provides methods for screening compounds for the capacity to disrupt binding between the sperm-specific protein kinase A anchoring protein of the invention and protein kinase A regulatory subunits, and methods for disrupting, inhibiting or preventing expression of this protein in developing sperm cells, spermatids or progenitor cells thereof, in order to provide male-specific contraception agents. Methods of male contraception, most preferably and advantageously readily reversible methods of male contraception, and methods for the prevention of pregnancy are provided by the use of compounds that disrupt, inhibit or prevent expression of the AKAP110 protein of the invention, whereby such compounds are detected or characterized using the methods of the invention. Advantageously, the invention also provides agents, preferably pharmaceutical agents, for effecting male contraception, most preferably comprising antisense oligonucleotides for inhibiting or preventing expression of AKAP1 10 in sperm cells, spermatids and progenitors thereof, and peptides and small molecules for disrupting AKAP 110/PKA RII binding in said cells.

Specific preferred embodiments of the present invention will become evident from the following more detailed description of certain preferred embodiments and the claims.

DESCRIPTION OF THE DRAWINGS

FIG. 2 is a sequence alignment of human (SEQ ID NO:15), bovine (SEQ ID NO:13), and murine (SEQ ID NO:11), AKAP110 amino acid sequences. Shaded areas indicate sequence identity between at least two of the three species.

FIG. 5A is a amino acid sequence alignment of RII binding domains of a variety of AKAP proteins: AKAP110 (Seq. ID No. 19); AKAP82 (Seq. ID No. 20); S-AKAP84 (Seq. ID No. 21); TAKAP80 (Seq. ID No. 22); MAP2 (Seq. ID No. 23); Ht31 (Seq. ID No. 24); AKAP150 (Seq. ID No. 25); AKAP75 (Seq. ID No. 26); AKAP92 (Seq. ID No. 27); AKAP120 (Seq. ID No. 28); AKAP220 (Seq. ID No. 29); Gravin (Seq. ID No. 30); AKAP-KL (Seq. ID No. 31); AKAP18 (Seq. ID No. 32) and Ezrin (Seq. ID No. 33). Shaded residues are conserved in a majority of the 15 aligned sequences.

FIG. 8A shows hybridization to frozen cryosection of mouse testis. "L" indicates the seminiferous tubule lumen; "RS" represents round spermatids of the seminiferous epithelium. Dotted lines represent boundaries between adjacent seminiferous tubules. FIG. 8B represents a higher-magnification view of a single seminiferous tubule hybridized with antisense AKAP110 probe. The bracketed areas represent the basal region of the seminiferous epithelium, containing spermatogonia, spermatocytes and Sertoli cells. "LS" represents late spermatids adjacent to the tubule lumen. Hybridization is detected only in the RS region of this section. FIG. 8C is in situ hybridization performed using a sense AKAP110 probe; no hybridization was detected.

FIGS. 9A and 9B are matched phase-contrast (FIG. 9A) and immunofluorescence (FIG. 9B) photomicrographs of caudal epididymal spermatozoa. The bar at the upper left-hand corner labeled "A" equals 15 μM. "F" indicates sperm flagella, "H" indicates sperm heads, "AC" indicates acrosomal segments, and "AC*" represents acrosomal caps released from the sperm heads. Inserts labeled "B " and "B" are phase-contrast and immunofluorescence photomicrographs incubated with preimmune serum.

DETAILED DESCRIPTION OF THE PREFERRED EMBODIMENTS

Figure 1:
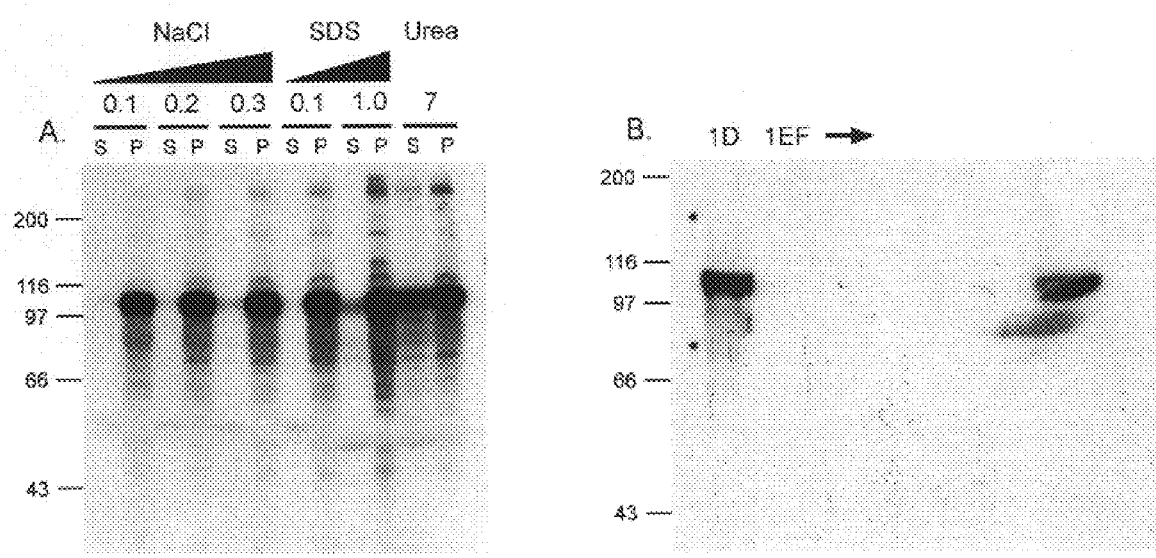
FIGS. 1A and 1B illustrate one- (FIG. 1A) and two-dimensional (FIG. 1B) gel electrophoretic analyses of extracted bovine sperm proteins. Numbering in the left-hand side of each Figure are molecular weight markers (in kilodaltons). Electrophoresis in each of the Figures in the vertical direction is SDS/PAGE; electrophoresis in the horizontal direction in FIG. 1B is isoelectric focusing, performed between pH 10 and pH 3 (arrayed left-to-right in the Figure). Paired lanes in FIG. 1A are labeled "S" for supernatant and "P" for pellet, as described in Example 1. The arrow in FIG. 1B denotes the position of the protein band excised for microsequencing analysis as described in Example 1.

The terms "mammalian sperm-specific protein kinase A anchoring protein having an apparent molecular weight of about 110 kildaltons" and "AKAP110" as used herein are intended to encompass proteins having the biological activity of any of the sperm-specific protein kinase A anchoring proteins disclosed herein or PKA-RII subunit-binding fragments thereof. This definition is also intended to encompass natural allelic variations in the sperm-specific protein kinase A anchoring protein-encoding sequences of the invention. Cloned nucleic acid provided by the present invention encodes sperm-specific protein kinase A anchoring proteins of any species of origin, including, for example, mouse, cow, horse, pig, rat, rabbit, dog, cat, and human, but preferably the nucleic acid provided by the invention encodes sperm-specific protein kinase A anchoring protein including the murine (SEQ ID Nos.: 11 and 12), bovine (SEQ ID Nos.: 13 and 14), and human (SEQ ID Nos.: 15 and 16) homologues. In addition, sequence alignment of the nucleic acid sequences of the murine (SEQ ID No. 11), bovine (SEQ ID No. 13) and human (SEQ ID No. 15) sequences provides one of ordinary skill in the art with sufficient information to be able to identify a nucleic acid probe wherein the sequence (or the amino acid sequence encoded therein) between the three mammalian species are identical. Such a sequence provides the skilled artisan with a probe that is useful for isolating a nucleic acid encoding AKAP110 from any mammalian species. Thus, this invention provides a plurality of consensus sequences for probe production, wherein said probes are useful for isolation or detection of AKAP110 genes or gene expression from any mammalian species.

The production of proteins such as the sperm-specific protein kinase A anchoring protein of the invention from cloned genes by genetic engineering means is well known in this art. The discussion which follows is accordingly intended as an overview of this field, and is not intended to reflect the full state of the art.

Nucleic acid encoding the sperm-specific protein kinase A anchoring proteins of this invention can be obtained, in view of the instant disclosure, by chemical synthesis, by screening reverse transcripts of mRNA from testis cells or cultured cell lines derived therefrom, by screening genomic libraries from appropriate cells, or by combinations of these procedures, as illustrated below. Screening of cDNA prepared from cellular mRNA or genomic DNA may be carried out with full-length, partial or oligonucleotide probes generated from the sperm-specific protein kinase A anchoring protein nucleotide sequence information provided herein, as discussed above. Probes may be labeled with a detectable group such as a fluorescent group, a radioactive atom or a chemiluminescent group in accordance with known procedures and used in conventional hybridization assays, as described in greater detail in the Examples below. In the alternative, sperm-specific protein kinase A anchoring protein encoding nucleic acid can be obtained by use of the polymerase chain reaction (PCR) procedure, with the PCR oligonucleotide primers being produced from the sperm-specific protein kinase A anchoring protein nucleotide sequences provided herein. See U.S. Pat. No. 4,683,195 to Mullis et al. and U.S. Pat No. 4,683,202 to Mullis. In addition, consensus proteins comprising artificially produced and/or genetically engineered proteins encoding at each sequence position an amino acid comprising the "consensus" between the nucleic acid sequences identified as Seq. ID Nos. 11, 13 and 15 are also provided by the invention.

Nucleic acids and oligonucleotides of the present invention are useful as probes for screening DNA libraries to isolate and characterize additional mammalian homologues of the sperm-specific protein kinase A anchoring protein-encoding nucleic acids of the invention. For the purposes of this invention, these probes are used under high stringency hybridization conditions, defined herein as follows. The probes are labeled with 150 $\mu$Ci $^{32}$P-ATP and hybridized overnight at 42° C. in a hybridization buffer comprising 6×SSC (0.9M NaCl, 0.09M sodium citrate dihydrate (pH 7.0)), 2×Denhardt's solution (0.04% Ficoll, 0.04% polyvinylpyrrolidone, 0.04% bovine serum albumin), and 0.25% sodium dodecyl sulfate (SDS). After hybridization, filters are washed four or five times for ten minutes apiece in an excess volume of 6×SSC (0.9 M NaCl, 0.09M sodium citrate dihydride, pH 7.0) and 0.05% SDS at room temperature. Thereafter, three ten-minute washes are performed one after another in this buffer at temperatures of 55° C., 60° C. and 63° C.

Sperm-specific protein kinase A anchoring proteins may be synthesized in cells, most preferably cells comprising exogenously-added, recombinant DNA, most preferably cDNA, encoding said proteins. In particular, cells transformed with a recombinant expression construct comprising a nucleic acid encoding a sperm-specific protein kinase A anchoring protein of the invention can be used to provide a homogeneous culture of sperm-specific protein kinase A anchoring protein expressing cells. Recombinant expression constructs comprising the sperm-specific protein kinase A anchoring protein coding sequences as disclosed herein can also be comprised of a vector that is a replicable DNA construct. Vectors are used herein either to amplify DNA encoding a sperm-specific protein kinase A anchoring protein and/or to express DNA which encodes a sperm-specific protein kinase A anchoring protein. For the purposes of this invention, a recombinant expression construct is a replicable DNA construct in which a DNA sequence encoding a sperm-specific protein kinase A anchoring protein is operably linked to suitable control sequences capable of effecting the expression of the receptor in a suitable host cell. The need for such control sequences will vary depending upon the host selected and the transformation method chosen. Generally, control sequences include a transcriptional promoter, an optional operator or enhancer sequence to control or regulate transcription, a sequence encoding suitable mRNA ribosomal binding sites, and sequences which control the termination of transcription and translation, and in mammalian cells, sequences that direct 5' terminal capping and 3' terminal polyadenylation of the primary transcript. Amplification vectors, on the other hand, do not require expression control domains. All that is needed is the ability to replicate in a host, usually conferred by an origin of replication, and a selection gene to facilitate recognition of transformants. See, Sambrook et al., 1990, MOLECULAR CLONING: A LABORATORY MANUAL (Cold Spring Harbor Press: New York).

Vectors useful for practicing the present invention include plasmids, viruses (including phage), retroviruses, and particularly integratable DNA fragments (i.e., fragments integratable into the host genome by recombination). The vector may replicate and function independently of the host genome, or more preferably, may, in some instances, integrate into the genome itself. Suitable vectors will contain replicon and control sequences which are derived from species compatible with the intended expression host. Transformed host cells are preferably prokaryotic or eukaryotic cells which have been transformed or transfected with recombinant expression constructs made using recombinant DNA techniques and comprising mammalian sperm-specific protein kinase A anchoring protein-encoding sequences. Preferred host cells are bacterial cells, most preferably *Escherichia coli* cells. Transformed host cells are chosen that are capable of expressing functional sperm-specific protein kinase A anchoring protein introduced using the recombinant expression construct. See, Sambrook et at., ibid.

Homogenous compositions of the mammalian sperm-specific protein kinase A anchoring proteins are provided by the invention. As used herein, the term "homogenous" is intended to encompass preparations wherein the mammalian sperm-specific protein kinase A anchoring protein of the invention is the predominant protein species in the preparation, preferably wherein the mammalian sperm-specific protein kinase A anchoring protein comprises at least 70%, more preferably wherein the mammalian sperm-specific protein kinase A anchoring protein comprises from 80–90%, and most preferably where the mammalian sperm-specific protein kinase A anchoring protein comprises greater than 90% of the protein in the preparation. In preferred embodiments, said preparations have one or a multiplicity of additional protein components wherein no one component comprises more than about 5% and more preferably about 1% of the protein in the preparation.

The invention also provides antibodies that are immunologically reactive to a mammalian sperm-specific protein kinase A anchoring protein, most preferably the bovine, murine or human homologues explicitly disclosed herein. The antibodies provided by the invention are raised in animals by inoculation with homogenous preparations of a mammalian sperm-specific protein kinase A anchoring protein of the invention or epitopes thereof, using methods well known in the art. Alternatively, peptide fragments of the mammalian sperm-specific protein kinase A anchoring protein of the invention can be chemically synthesized or isolated from the full-length sequence, covalently attached to a carrier molecule such as keyhole limpet hemocyanin, and injected into an appropriate experimental animal. Animals that are used for such inoculations include individuals from species comprising cows, sheep, pigs, mice, rats, rabbits, hamsters, goats and primates. Preferred animals for inoculation are rodents (including mice, rats, and hamsters) and rabbits. For preparing polyclonal antisera, the most preferred animal is rabbit. For preparing monoclonal antibodies, the most preferred animal is the mouse.

Cells that can be used for such inoculations, or for any of the other means used in the invention, include any cell, clonal isolate or cell line that expresses a mammalian sperm-specific protein kinase A anchoring protein or any epitope thereof, most preferably as a result of molecular or genetic engineering. Preferred cells for preparing said recombinant protein is $E.$ $coli$ cells, most preferably having been transformed with a recombinant expression construct comprising a nucleic acid encoding a human, bovine or murine sperm-specific protein kinase A anchoring protein or epitopes thereof, and that express the mammalian gene product, wherein it is understood that such preparations are sufficiently purified from pyrogenic or other bacterial toxins or contaminants as to be suitable for injection into an animal.

The present invention provides polyclonal antisera and monoclonal antibodies that are immunologically reactive with an epitope that is a mammalian sperm-specific protein kinase A anchoring protein or fragment thereof. These antibodies are made using methods and techniques well known to those of skill in the art.

Monoclonal antibodies provided by the present invention are produced by hybridoma cell lines, that are also provided by the invention and that are made by methods well known in the art. Hybridoma cell lines are made by fusing individual cells of a myeloma cell line with spleen cells derived from animals immunized with a mammalian sperm-specific protein kinase A anchoring protein, or cells expressing such a mammalian sperm-specific protein kinase A anchoring protein, preferably the murine, bovine or human sperm-specific protein kinase A anchoring protein, as described above. The myeloma cell lines used in the invention include lines derived from myelomas of mice, rats, hamsters, primates and humans. Preferred myeloma cell lines are from mouse, and the most preferred mouse myeloma cell line is P3X63-Ag8.653. The animals from whom spleens are obtained after immunization are rats, mice and hamsters, preferably mice, most preferably Balb/c mice. Spleen cells and myeloma cells are fused using a number of methods well known in the art, including but not limited to incubation with inactivated Sendai virus and incubation in the presence of polyethylene glycol (PEG). The most preferred method for cell fusion is incubation in the presence of a solution of 45% (w/v) PEG-1450. Monoclonal antibodies produced by hybridoma cell lines can be harvested from cell culture supernatant fluids from in vitro cell growth; alternatively, hybridoma cells can be injected subcutaneously and/or into the peritoneal cavity of an animal, most preferably a mouse, and the monoclonal antibodies obtained from blood and/or ascites fluid.

Monoclonal antibodies provided by the present invention are also produced by recombinant genetic methods well known to those of skill in the art, and the present invention encompasses antibodies made by such methods that are immunologically reactive with an epitope of a mammalian sperm-specific protein kinase A anchoring protein.

The present invention encompasses fragments of the antibody that are immunologically reactive with an epitope of a mammalian sperm-specific protein kinase A anchoring protein. Such fragments are produced by any number of methods, including but not limited to proteolytic cleavage, chemical synthesis or preparation of such fragments by means of genetic engineering technology, and include Fab fragments, Fab' fragments, $F(ab)_2$ fragments, and $F_v$ fragments. The present invention also encompasses single-chain antibodies that are immunologically reactive with an epitope of a mammalian sperm-specific protein kinase A anchoring protein made by methods known to those of skill in the art. In preferred embodiments, the mammalian sperm-specific protein kinase A anchoring protein is a bovine, murine or human homologue as provided by the invention.

The present invention also encompasses an epitope of a mammalian sperm-specific protein kinase A anchoring protein that is comprised of sequences and/or a conformation of sequences present in the mammalian sperm-specific protein kinase A anchoring protein molecule. This epitope may be naturally occurring, or may be the result of proteolytic cleavage of the mammalian sperm-specific protein kinase A anchoring protein molecule and isolation of an epitope-containing peptide or may be obtained by chemical and more preferably automated chemical synthesis of an epitope-containing peptide using methods well known to those skilled in the art. The epitope also comprises a "consensus" epitope, wherein the identity of the amino acid residue at each position in the epitope sequence represents the "consensus" residue obtained by comparison of the amino acid sequences identified as Seq. ID Nos. 12, 14 and 16. The present invention also encompasses epitope peptides produced as a result of genetic engineering technology and synthesized by genetically engineered cells, preferably prokaryotic cells and most preferably $E.$ $coli$ cells.

The invention also provides methods for screening compounds for the capacity to disrupt binding between the mammalian sperm-specific protein kinase A anchoring proteins of the invention and protein kinase A, most preferably the RII subunit of protein kinase A. In these methods, homogenous preparations of both the mammalian sperm-specific protein kinase A anchoring protein of the invention and protein kinase A, preferably recombinant embodiments thereof and most preferably recombinant RII subunits thereof, are used to assay the effects of the screened compounds on AKAP-PKA binding. Preferably, the mammalian sperm-specific protein kinase A anchoring protein of the invention or protein kinase A, most preferably said RII subunit thereof, are detectably labeled, which for the purposes of this aspect is intended to encompass but not be limited to radioactive, fluorescent and antigenic labels. In other preferred embodiments, the mammalian sperm-specific protein kinase A anchoring protein of the invention or protein kinase A, most preferably said RII subunit thereof, are immobilized to a substrate. For the purposes of this disclosure, the term "substrate" is intended to encompass solid platforms such as are used as understood by those with skill in the art in enzyme-linked immunosorbent assay ("ELISA") and radioimmune assay ("RIA") wells and the wells of plastic 96-well plates, and in addition beads and chromatographic substrates. In certain embodiments, the methods are performed as variants of the RII overlay method described herein below. In alternative embodiments, particularly suited for high throughput screening and automation, the methods are performed to resemble ELISA and RIA assays, whereby at least one of either the mammalian sperm-specific protein kinase A anchoring protein of the invention or protein kinase A are immobilized to a solid support. In preferred embodiments of each of these aspects of the methods of the invention, either the mammalian sperm-specific protein kinase A anchoring protein of the invention or protein kinase A is detectably labeled. The invention also provides the agents and compounds detecting using these methods that are capable of disrupting AKAP: PKA RII binding.

The invention also provides methods for inhibiting or preventing expression of the mammalian sperm-specific protein kinase A anchoring protein of the invention in sperm, spermatids or progenitor cells thereof, said methods comprising introducing an antisense oligonucleotide into said cell. Said methods further comprise screening candidate oligonucleotides in recombinant cells, most preferably mammalian cells, transformed with a recombinant expression construct of the invention encoding a mammalian sperm-specific protein kinase A anchoring protein as disclosed herein, and assaying said cell in the presence and absence of the candidate oligonucleotide for recombinant gene expression. The invention also provides the oligonucleotides detected using these methods that are capable of inhibiting or preventing recombinant AKAP expression.

The Examples which follow are illustrative of specific embodiments of the invention, and various uses thereof. They set forth for explanatory purposes only, and are not to be taken as limiting the invention.

EXAMPLE 1

Isolation and Characterization of Bovine AKAP110 Protein from Bovine Sperm

In order to derive a probe for isolating cDNA encoding an anchoring kinase A protein having an apparent molecular weight of 110kD (AKAP110) in sperm, AKAP110 protein was isolated from bovine sperm as follows.

Testes from mature bulls with intact tunica were obtained from a local slaughterhouse and sperm from caput or caudal epididymis were isolated and washed as described in Vijayaraghavan et al. (1985, *Biol. Reproduc.* 32: 489–500). The washed sperm were fractionated into heads, tails and midpieces as described in Mohapatra et al. (1998, *Biochem. Biophys. Res. Commun.* 244: 540–545). Tails were pelleted at 16,000×g for 15 min and resuspended in homogenization buffer (HB) comprising 50 mM Tris-HCl (pH 7.0), 2 mM EGTA, 2 mM EDTA, 0.5M NaCl, 1% Nonidet P-40 (NP-40), 0.1% β-mercaptoethanol, 10 mM benzamidine, 1mM phenylmethylsulfonyl fluoride (PMSF), 1mM dithiothreitol (DTT), 10 μg/mL trypsin inhibitor, 10 μg/mL leupeptin, 1 μg/mL aprotinin and 1 μg/mL Nα-p-tosyl-L-lysine chloromethyl ketone (TLCK; all chemicals obtained from Sigma Chemical Co., St. Louis, Mo.). The resuspended tails were sonicated in HB for 20 sec at a setting of "4" on a Branson Sonifer 450. The sonicated suspension was inverted for 30 min at 4° C. and then centrifuged at 16,000×g for 15 min at 4° C. The pellet was then resuspended in HB, inverted for 30 min at 4° C., and then again centrifuged at 16,000 rpm for 15min at 4° C. Finally, the pellet was resuspended in Sonication Buffer (SB) comprising 9M deionized urea, 4% NP-40, 2% ,-mercaptoethanol, and 2% ampholytes pH 3–10 (obtained from Pharmacia LKB, Upsala, Sweden) and rocked at room temperature for 2h. This mixture was then used for two-dimensional electrophoresis as described below.

The identity of AKAP110 in the extracts prepared as described above was determine using an RII overlay assay. This assay was based on previous experiments which had shown that PKA anchoring proteins could be specifically detected after electrophoretic separation by overlay with labeled RII subunit of mammalian PKA (see Vijayaraghavan et al., 1997, *J. Biol. Chem.* 272; 4747–4752). These assays were performed as follows. Polyacrylamide gel electrophoresis containing sodium dodecyl sulfate (SDS/PAGE) was performed as described in Johnson et al. (1997, *Devel. Biol.* 192: 340–350) and Visconti et al. (1997, *Devel. Biol.* 192: 351–363). Approximately 50k,g protein per lane was loaded on a 10% gel and electrophoresed overnight at a constant current of 8mA. After electrophoresis, protein bands were transferred to Immobilon P (polyvinylidene difluoride, obtained from Millipore, Bedford, Mass.) as described in the Johnson and Visconti references. After about 1h, blot transfer was complete, and the blots were pre-treated in a solution containing 10 mM Tris-HCl (pH 7.5), 150 mM NaCl, 5% non-fat milk, and 0.1% BSA (termed BLOTTO buffer) to prevent non-specific binding to the membrane. The blot was then treated with $^{32}$p labeled RIIα protein at a concentration of 500,000 cpm/mL in BLOTTO buffer. Recombinant RIIα (prepared by expression in *E. coli* as described above; see Carr et al., 1991, *J. Biol. Chem.* 266: 14188–14193) was radiolabeled by incubation with the catalytic subunit of PKA in the presence of γ-$^{32}$P-labeled ATP. Approximately 1 μg of catalytic subunit was added to 5 μg of RII plus 50 μCi of $^{32}$P-ATP in a buffer consisting of 0.05M MOPS (pH 7.0), 0.01M MgCl$_2$, 0.25mg/mL bovine serum albumin (BSA) and 0.01M dithiothreitol (DTT) and incubated for one hour at room temperature. The radiolabeled RII was then separated from the radiolabeled ATP using a KWIK-Sep™ exocellulose desalting column (Pierce Chemical, Rockford, Ill.) following the manufacturer's instructions. After incubation of the blot for four hours at room temperature, the blot was washed four times for fifteen minutes each with an excess volume of TTBS (0.1% Tween-20, 10 mM Tris-HCl, pH 7.5, 150 mM NaCl). Protein bands on the blot radiolabeled by binding to the $^{32}$P labeled RIIα were then visualized by autoradiography by exposure to X-ray film (Kodak XAR, Eastman Kodak, Rochester, N.Y.) overnight at −80° C.

The results of one such experiment are shown in FIGS. 1A and 1B. FIG. 1A shows SDS/PAGE analysis of tail fractions extracted in HB containing 0.1, 0.2 or 0.3M NaCl (lanes 1, 2 and 3 of the Figure), 0.3M NaCl plus 0.1 or 1% SDS (lane 4 and 5), or 0.3M NaCl, 1% SDS and 7M urea (lane 6), followed by blotting and radioactive RII overlay analysis as described. (In these experiments, the HB lacked 0.5M NaCl and 1% NP-40.) These experiments illustrate the insolubility of AKAP110 protein in bovine sperm under the extraction conditions employed in these assays; the majority of the protein is seen to remain in the pellet even after extraction in high salt and/or detergent concentrations.

FIG. 1B shows the results of two-dimensional assay comprising isoelectric focusing (IEF) in the first (horizontal) dimension and SDS/PAGE in the second (vertical) dimension. These assays were performed only on sperm that had been subjected to the final extraction step using SB buffer described above. IEF was performed using standard protocols as described in Bollag & Edelstein (1991, PROTEIN METHODS, Wiley-Liss, N.Y.) using ampholytes spanning a pH range of 3–10, and SDS/PAGE was performed as described above. The results of these assays showed that AKAP110 was solubilized only by treatment with high concentrations of urea (9M).

A band on a gel processed in parallel and corresponding to the position of AKAP110 detected in the two-dimensional assay as described was excised and the AKAP110 protein eluted therefrom. This protein was subjected to tryptic digestion, high pressure liquid chromatographic separation, and amino acid microsequencing. As a result, seven peptide fragments were sequenced; these sequences are as follows:

SCVETLGEHIIK (Seq. ID No.: 1);
KGFCVDYYNTT (Seq. ID No.: 2);
EGISACLQGSPFVTP (Seq. ID No.: 3);
SPAVSHESSLR (Seq. ID No.: 4);
NLLSETIFK (Seq. ID No.: 5);
GTGTAETFLQNAYQAIHNEL (Seq. ID No.: 6); and
LLQLSAAAVEK (Seq. ID No.: 7).

These sequences were compared with sequences in GenBank and were determined to be unique. However, certain of these peptides (SEQ ID Nos. 6 and 7) showed approximately 90% sequence similarity to expressed sequence tags (ESTs) previously isolated from mouse and human testis-specific cDNA libraries. These included ESTs designated MTEST21 (C. Hoog, Department of Molecular Genetics, Karolinska Institute, Stockholm, Sweden), AA424242 (available royalty-free from Lawrence Livermore National Laboratory), AA92960 (available royalty-free from Lawrence Livermore National Laboratory) and AA061683 (Genbank, National Center for Biotechnology Information, Bethesda, Md.). These similarities, and the uniqueness of the peptide sequences specific for bovine testis AKAP110, were used to develop probes for the library screening experiments described in Example 2.

EXAMPLE 2

Isolation and Characterization of cDNA encoding Murine AKAP110 Protein

The results obtained in Example 1 were used to develop AKAP110-specific probes for screening a murine CDNA library for sequences encoding AKAP110.

Two of the EST sequences identified as being similar to two of the seven peptide sequences derived from bovine AKAP110 protein were used. These ESTs, AA92960 and AA061683, had the following nucleotide sequence: AA92960: ATGAGTGCAAACTTAAGTCTCCTCCCCA-CAAGATATGTGACCAAGAACAAAC AGAAAA-GAAAGATCTGATGAGTGTCATCT-TCAATTTTATCCGGAACTTACTC AGCGAGACCATATTCAAGAGTAGCCG-TAACTGTGAATCCAATGTGCATGAG CAGAACACT-CAGGAAGAAGAGATACACCCGTGT-GAAAGGCCTAAGACTCCA TGTGAAAGGCCTATTACCCCGCCTGC-CCCGAAATTCTGTGAGGATGAGGAGG CCACTG-GTGGTGCCTTATCTGGGCTAACCAA-GATGGTTGCCAACCAGCTAGA CAACTGTATGAATGGGCAGATGGTGGAG-CACCTGATGGACTCGGTGATGAA GTTATGCCTCAT-TATTGCCAAGTCCTGTGACTCTCCCCT-GTCGGAGCTGGGA GAGGAAAAGTGTGGGGATG (Seq. ID No.: 8); and AA061683: GTGAATCCAATGTG-CATGAGCAGAACACTCAGGAAGAAGAGATACAC CCGTGTGAAAGGCCTAAGACTCCATGT-GAAAGGCCTATTACCCCGCC TGCCCCGAAATTCT-GTGAGGATGAGGAGGCCACTGGTGGTGCCTTAT CTGGGCTAACCAAGATGGTTGCCAAC-CAGCTAGACAACTGTATGAAT GGGCAGATGGTG-GAGCACCTGATGGACTCGGTGATGAAGTTATGCCT CATTATTGCCAAGTCCTGTGACTCTC-CCCTGTCGGAGCTGGGAGAGGA AAAGTGTGGG-GATGCCAGCCGGCCAAATTCTGCCTTC-CCAGATAACT TATATGAGTGCCTACCAGTCAAGGGCA-CAGGGACAGCTGAAGCCCTC CTGCAGAACG (Seq. ID No.: 9).

These oligonucleotides were obtained from Research Genetics Inc. (Huntsville, Ala.). and radiolabeled by end-labeling with $^{32}$P using terminal transferase (obtained from New England Biolabs, Beverly, Mass.) in the presence of $\gamma^{32}$P-ATP under conditions recommended by the supplier. Radiolabeled probes were used to screen a mixed germ cell mouse testis cDNA library prepared in the cloning vector Lambda ZAP, obtained from Stratagene (LaJolla, Calif.). Approximately 500,000 phage plaques were screened using conventional techniques (Sambrook et al., ibid.). The probes were labeled with 150 µCi $^{32}$P-ATP and hybridized overnight at 42° C. in a hybridization buffer comprising 6×SSC (0.9M NaCl, 0.09M sodium citrate dihydrate (pH 7.0)), 2×Denhardt's solution (0.04% Ficoll, 0.04% polyvinylpyrrolidone, 0.04% bovine serum albumin), and 0.25% SDS. After hybridization, the filters were washed four or five times for ten minutes apiece in an excess volume of 6×SSC (0.9 M NaCl, 0.09M sodium citrate dihydride, pH 7.0) and 0.05% SDS at room temperature. Thereafter, three ten minute washes were performed one after another in this buffer at temperatures of 55° C., 60° C. and 63° C. Three positively-hybridizing clones were identified and plaque-purified. Insert were excised from the phage vector in vitro to provide pBluescript SK plasmids containing the inserts using an excision technique according to the manufacturer's instructions (Stratagene).

Inserts were amplified by the polymerase chain reaction for 25 cycles consisting of 30 sec at 94° C., 30 sec at 55° C. and 2 min at 72° C. using primers complementary to the pBluescript SK vector on either side of the insert (Stratagene). Amplification using the three plasmids derived from the three positively-hybridizing phage resulted in amplification products of 2.5 kb, 2.5 kb and 3.1 kb. Nucleotide sequence determination was performed using Taq polymerase (in a kit supplied by Applied Biosystems, Foster City, Calif.) by the dideoxynucleotide chain termination method (Sanger et al., 1977, *Proc. Natl. Acad. Sci.* USA 74: 5463–5467). The sequences of these inserts were overlapping, with the 3.1 kb insert containing an additional 600bp of sequence information 5' to the sequences contained in the other insert fragments. In the largest clone, an initiation Met codon is located at nucleotide residue 292, and the context of this initiation codon (residues 289–294: AGGATGG) indicates that it is a translation start site (Kozak, 1987, *Nucleic Acids Res.* 15: 8125–8148). The 288 residues 5' to this putative translation start site contain 10 inframe translation termination codons, precluding the use of another contiguous ATG codon upstream. In addition, the sequence between nucleotide residue 292 and residue 2887 comprised an open reading frame encoding a protein having 864 amino acids; residues 2884–2886 encoded a translation termination codon followed by a polyA tail at residue 3079. This 3.1 kb insert was cloned into plasmid pET30A (obtained from Novagen, Madison, Wis.) after digestion with EcoRi and XhoI using conventional techniques.

Figure 2B:
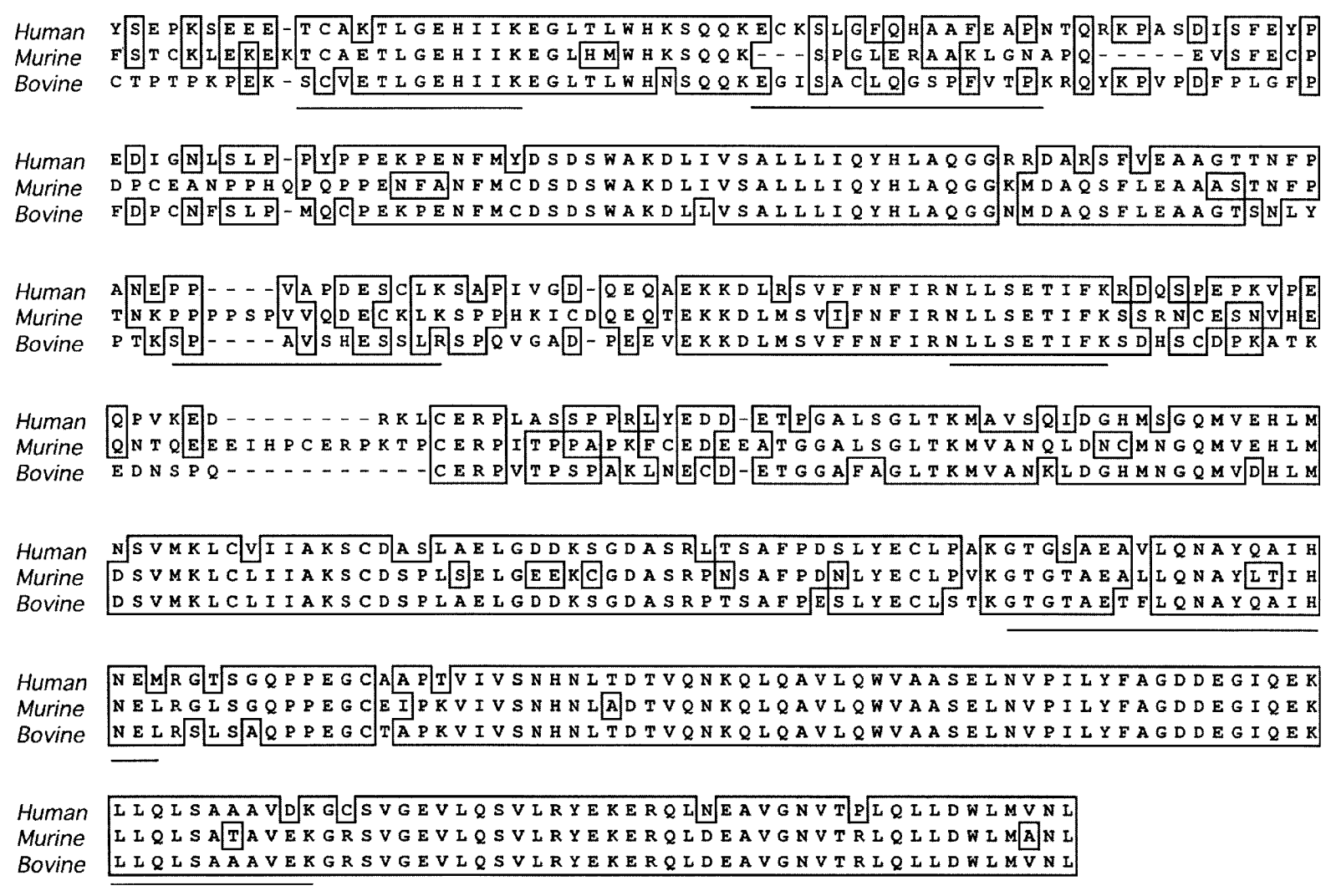

The sequence of the 3.1 kb fragment is shown in FIG. 2 and comprises Seq ID Nos. 10 and 11. These sequences have been deposited with GenBank under accession number AF093406.

EXAMPLE 3

Isolation and Characterization of cDNA encoding Bovine and Human AKAP110 Protein The bovine and human homologues of the mouse AKAP110 protein-encoding cDNA described in Example 2 above were obtained as follows.

The mouse AKAP cDNA was used as a probe to screen a bovine oligo dT-primed cDNA library prepared in the Lambda ZAPII vector and obtained from Stratagene. 700,000 clones were screened at high stringency as described above using the 3.1 kb insert $^{32}$P-labeled by the random primer method (Sambrook et al., ibid.). This screening resulted in 12 positively-hybridizing plaques that were plaque-purified and converted to pBluescript plasmids as described above. Nucleotide sequencing of these plasmids revealed them to be a collection of overlapping fragments, the longest of which was 2.9 kb in length and contained all but the amino-terminal 4 amino acids of the complete bovine AKAP110-encoding sequence (when compared with the putative amino acid sequence of the murine clone). The bovine sequence is shown in FIG. 2 and Seq ID Nos. 12 and 13. All seven of the peptides produced by microsequencing the bovine AKAP110 protein as described in Example 1 were found in the predicted bovine amino acid sequence. These sequences have been deposited with GenBank under accession number AF093407.

The human AKAP110 cDNA was isolated from a human testis cDNA library obtained from Clontech (Palo Alto, Calif.) and was screened using the murine 3.1 kb fragment at high stringency as described for the screening of the bovine library. Several positively-hybridizing phage plaques were obtained and plaque purified, and the size of the hybridizing insert fragments determined by restriction enzyme digestion and Southern blot analysis (Sambrook et al., ibid.). The longest hybridizing insert was 1.3kb, which was sequenced and recognized to be too short to encode the complete 110 kD protein. The polymerase chain reaction-based RACE technique was used to obtain the missing portions of the sequence from testis cDNA (obtained from Clontech), the method being performed using a kit supplied by Clontech according to the instructions provided by the supplier.

The human sequence is shown in FIG. 2 and Seq ID Nos. 14 and 15. An initiation Met codon is located at nucleotide residue 230, and the 229 residues 5' to this putative translation start site contain 3 inframe translation termination codons. In addition, the sequence between nucleotide residue 230 and residue 2788 comprised an open reading frame encoding a protein having 853 amino acids; residues 2789–2791 encoded a translation termination codon. These sequences have been deposited with GenBank under accession number AF093408 .

EXAMPLE 4

Sequence Characterization and Comparison of cDNA encoding Murine, Bovine and Human AKAP110 Protein The amino acid sequences encoded by the three mammalian AKAP110 cDNA clones of the invention are aligned in FIG. 2; regions of sequence identity are represented as shaded in the Figure. This alignment was produced using the ClustalW Alignment program (MacVector Software, Oxford Molecular Group). The nucleotide sequence of the bovine clone predicted an amino acid sequence of 859 amino acids having a calculated molecular weight of 95,578 and a calculated isoelectric point of 6.02. These results were consistent with the experimentally-observed values obtained according to Example 1. There was 65% amino acid sequence identity among the three species (554 out of 864 identical residues). There were also large domains of greater than 95% sequence homology interspersed by regions where some amino acids were deleted in one sequence compared with the other two (for example, beginning at amino acid 45), as well as a region of significant sequence diversity (e.g., the 50 amino acids between residues 475 and 525). No matches to AKAP110 were found in the Prosite database of patterns (Bairoch et al., 1997, *Nucleic Acids Res.* 25: 217–221), except for patterns otherwise having a high probability of occurrence, such as phosphorylation sites. Finally, the SOSUI structural analysis computer program (Hirokawa et al., 1998, *Bioinformatics* 14: 378–379) predicts AKAP110 to be a soluble protein.

Figure 4A:
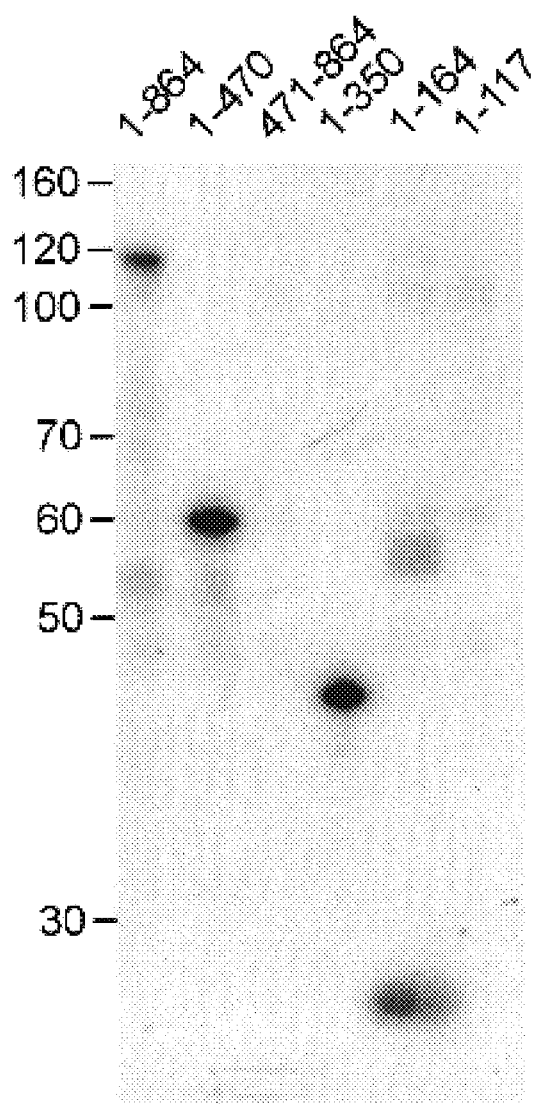
FIGS. 4A and 4B depict RII overlay (FIG. 4A) and Western blot assays (FIG. 4B) of identical blots containing full-length (1–864) and truncated fragments (1–470; 471–864; 1–350; 1–164; and 1–117) of murine AKAP110 protein expressed and isolated from E. coli.
Figure 4B:
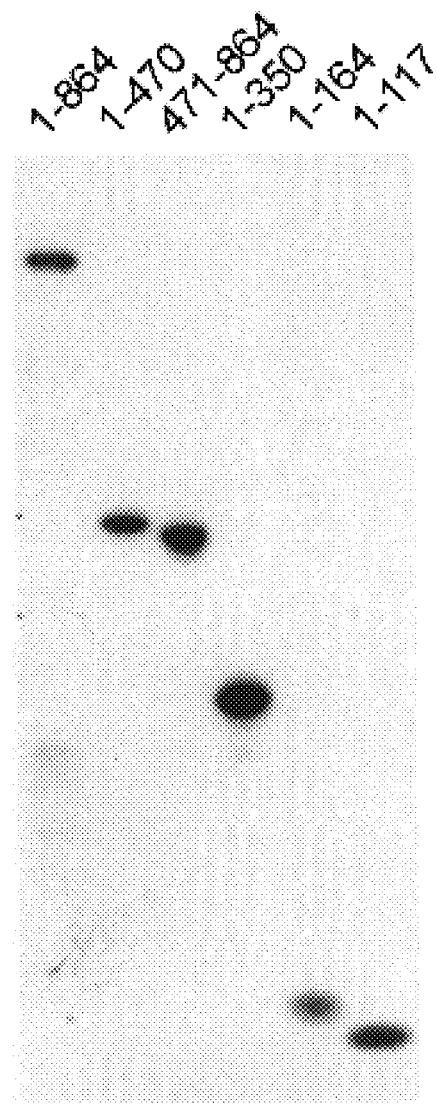
Figure 4C:
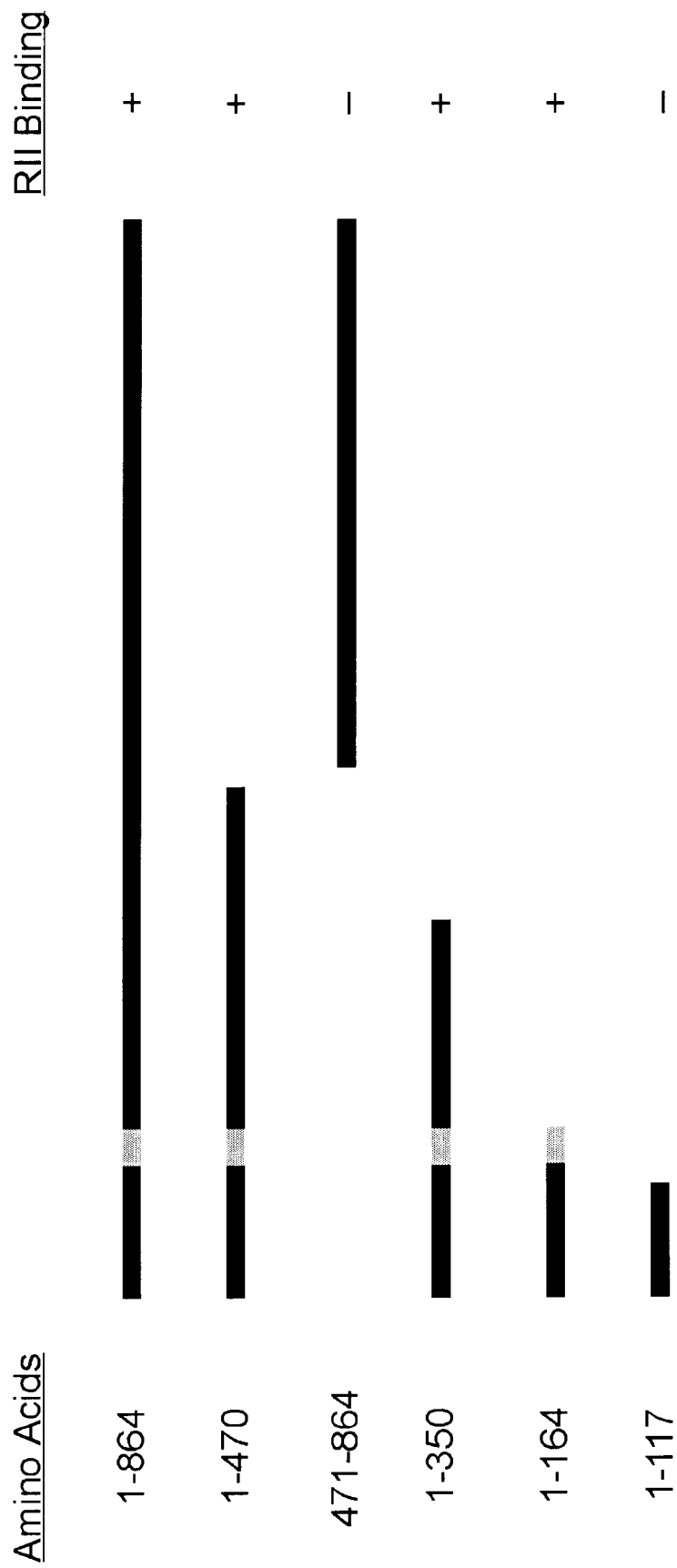
FIG. 4C is a schematic diagram of RII binding to AKAP110 and fragments thereof.

The conserved regions of sequence are expected to correspond to functional domains. The portion of the sequence corresponding to the RII binding domain was determined using an RII overlay assay as follows. The mouse cDNA was fragmented into the following species containing the indicated portions of the full-length AKAP 110 amino acid sequence: residues 1–470; 471–864; 1–350; 1–164; and 1–117. These fragments were subcloned into the pET30A vector (Novagen) and expressed in *E. coli* using a protocol provided by the supplier of the vector. The protein fragments were isolated from individual *E. coli* clones, separated by SDS/PAGE and transferred to an Immobilon P membrane as described above. This blot was then hybridized with $^{32}$P-labeled RIIα (results shown in FIG. 4A) or with horse radish peroxidase-conjugated S-protein that detects an S-tag expressed as a fusion protein by the pET30A vector (results shown in FIG. 4B). The results shown in FIG. 4B demonstrate the presence of all six fragments on the blot, while the results shown in FIG. 4A indicate that only certain of these fragments are capable of binding the radiolabeled RIIα protein. The pattern of RIIα binding of these fragments is summarized in FIG. 4C. Deletion of the carboxyl-terminal half of the protein (residues 471–864) had no effect on RII binding, while deletion of the amino terminal half (residues 1–470) abolished RII binding. Progressive continuation of this deletion analysis limited the region of the sequence to amino acids 117 and 164.

Figure 4D:
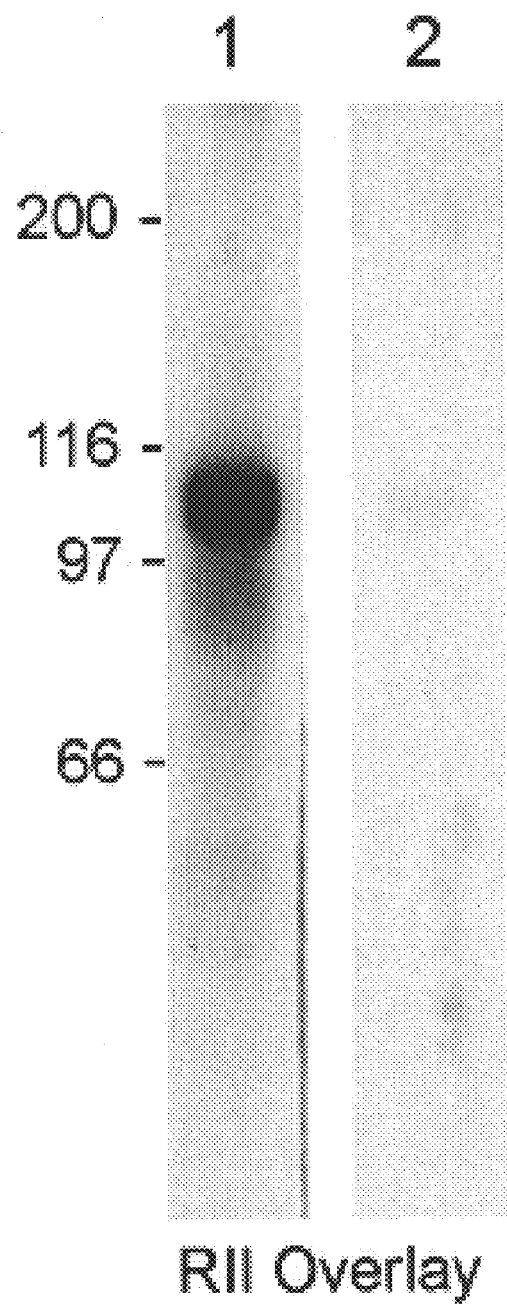
FIG. 4D depicts Western blot analysis performed in the absence (left-hand lane) or presence (right-hand lane) of the peptide used to prepare the antibody with which the Western blots were probed. Numbering in the left-hand side of the Figure represents molecular weight markers (in kilodaltons).

A comparison of the portion of the sequence delineated by this analysis and several prior art AKAP sequences implicated the sequence corresponding to amino acids 124–141 in the mouse sequence as being the RII binding site. The identity of this portion of the sequence as an RIIα binding site was confirmed by preparing a synthetic peptide having amino acid sequence:

SFYANRLTNLVI (Seq ID No.: 16) with an automated peptide synthesizer using 9-fluorenylmethoxycarbonyl (Fmoc) chemistry and base-mediated coupling (Applied Biosystems). This peptide was shown to prevent radiolabeled RIIα binding when it was included in the binding assay at a concentration of 1 µM. The results of these experiments are shown in FIG. 4D.

As a result of this alignment, a comparison was made between the RII binding domain of AKAP110 and the RII binding domains of 14 other known AKAP proteins; this alignment is shown in FIG. 5A. This alignment permitted the development of a model of the RII binding motif in AKAP proteins. Optimal alignment of the RII binding sequence from these fifteen proteins was performed using the ClustalW Alignment program (MacVector). The comparison was performed iteratively, wherein the sequences were compared and modified until a consensus sequence was obtained. This analysis revealed that 8 out of 18 positions were strongly conserved in this sequence. All of these conserved positions encoded predominantly hydrophobic amino acids. A common motif can be represented as follows:

X-{L/I/V}-X-X-X-{A/S}-X-X-{L/I/V}-{L/I/V}-X-X-{L/I/V}-{L/I/V}-X-X-{A/S}-L/I/V} (Seq ID No.: 17)

where "X" is any amino acid and the residues in brackets are alternative, conserved amino acids at that position in the consensus sequence. Eleven of the fifteen AKAPs aligned match at least 7 of the 8 conserved positions; if additional alternative residues are allowed (such as V for A/S and T, A or M for L/I/V, then nine of the fifteen AKAPs are conserved in all eight positions and 13 out of 15 are conserved at 7 of 8 positions. Six of the eight conserved positions consist of branched aliphatic residues that are most likely to be involved in binding hydrophobic amino acids at the amino terminus of the RII subunit (see Dell'Acqua & Scott, 1997, *J. Biol. Chem.* 272: 12881–12884). The other two positions (position 5 and 7) are occupied by either Ala or Ser, residues having low steric bulk, amphipathic or hydrophobically neutral and ambivalent in terms of placement either on the internal or external face of a protein. Positions 2 and 18 contain the most variability in the conserved residues, suggesting that these residues flank a more sequence-restricted central core.

Figure 5C:
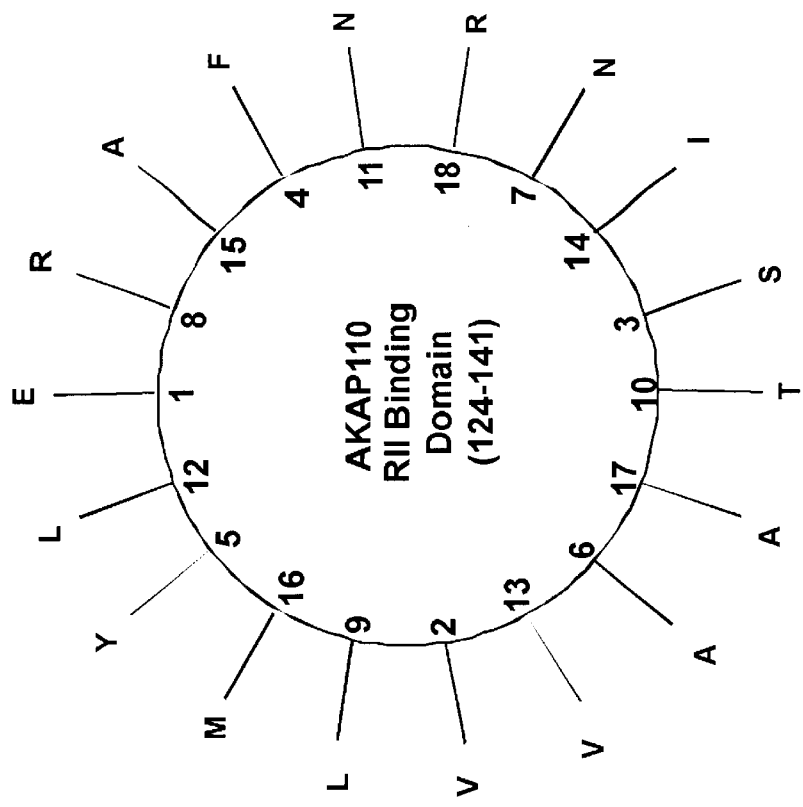
FIGS. 5B and 5C are schematic diagrams of helical wheel representations of the AKAP consensus sequence of the RII binding domain (FIG. 5B) and the AKAP 110 RII binding domain (FIG. 5C).
Figure 5B:
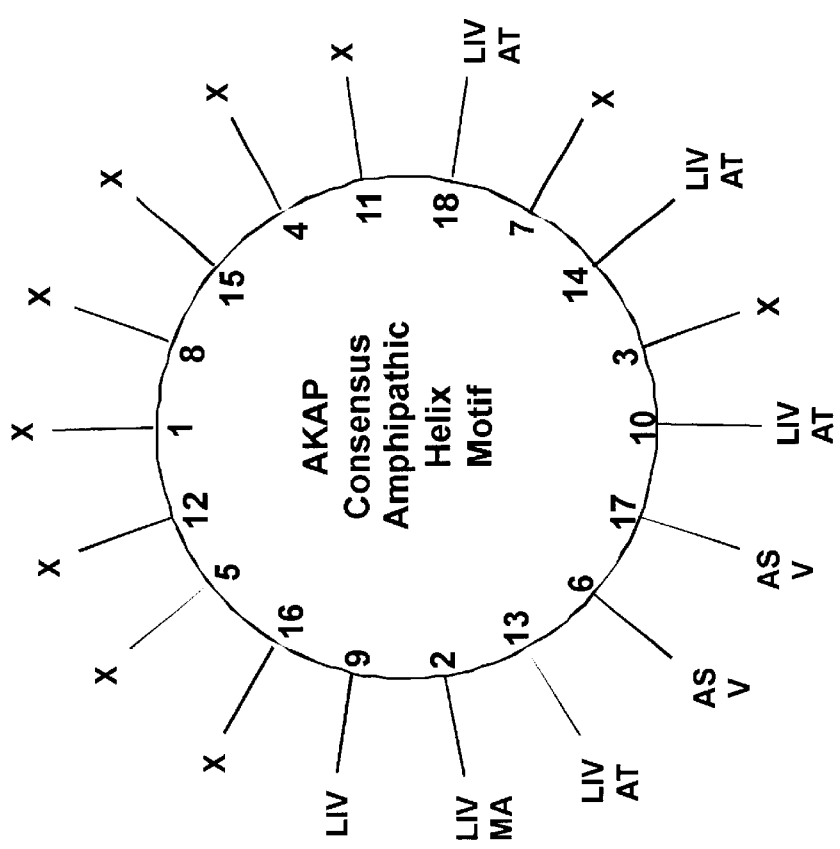

Arrangement of the residues in the consensus sequence into an alpha helical structure is shown in FIGS. 5B and 5C. When drawn in this way, all of the conserved positions are on one face of the helix (between residues 9 and 18 as shown). The residues between the conserved residues are predominantly hydrophilic neutral residues. These results are consistent with a model of AKAP:RII binding containing an amphipathic helix having a highly conserved, hydrophobic face and a less well conserved, hydrophilic face. The entire binding domains appears to encompass five turn of the alpha helix. It is expected that the affinity between any particular AKAP and RII pair will be related to how closely the AKAP binding domain matches the conserved motif, especially at positions (such as 6, 9, 10, 13, 14 and 17) in the middle of the domain. AKAP110 is conserved at all 6 of these central positions (as shown in FIG. 5C).

These results suggest methods for screening compounds for the ability to inhibit, modulate or enhance binding between AKAP110 and RIIα, as described in further detail herein.

Figure 6:
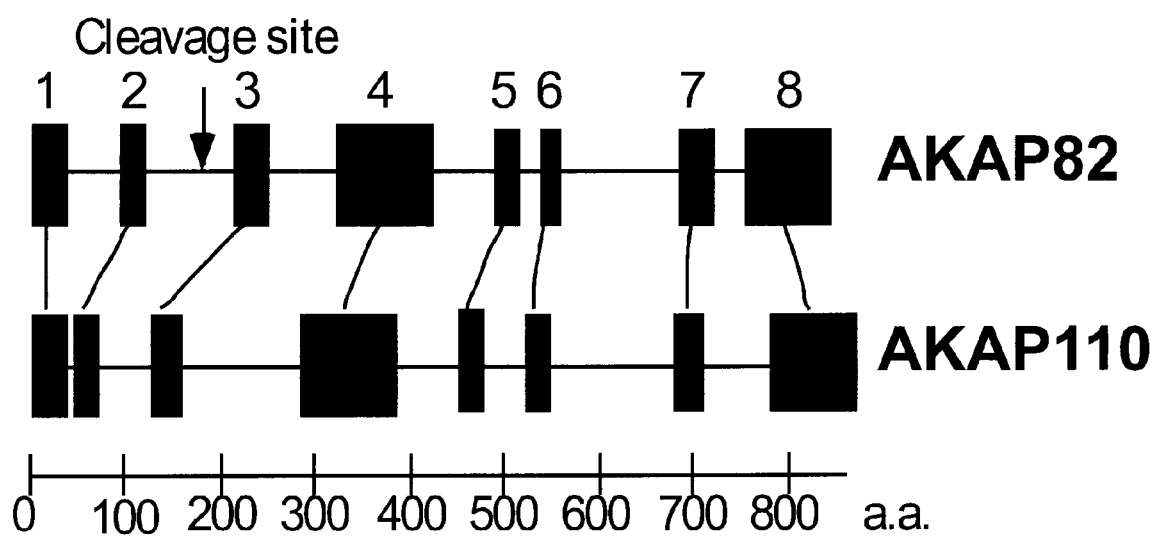
FIG. 6 is a schematic alignment of AKAP110 and AKAP82 amino acid sequences. The boxed regions represent portions of the amino acid sequence of at least 20 amino acids having greater than 50% sequence homology.

The murine, bovine and human AKAP110 sequences were used to search a number of databases for related amino acid sequences. No matches were found in the Prosite database (Bairoch et al., 1997, *Nucleic Acids Res.* 25: 217–221). Using the Gapped BLAST program (Altschult et al., 1990, *J. Molec. Biol.* 215: 403–410) from the National Library of Medicine at the National Institutes of Health, AKAP110 was found to have significant amino acid sequence homology to a previously-described sperm major fibrous sheet protein, variously termed AKAP82, p82, FSC-1 and H1 (see Carrera et al., 1994, *Develop. Biol.* 165: 272–284; Fulcher et al., 1995, *Biol. Reprod.* 52: 41–49; and Mohapatra et al., 1998, ibid.). Alignment using up to 20 gaps revealed 35% sequence identity between AKAP110 and AKAP82. This sequence similarity exists throughout the entire length of the protein molecule, although the longest continuous stretch of identity is 11 amino acids in length. The topography of the sequence similarities between AKAP110 and AKAP82 is illustrated in FIG. 6, where the boxes define conserved regions of sequence of at least 20 amino acids having greater than 50% homology. This comparison suggests that these proteins may share several conserved domains that may perform similar functions. Conversely over half the amino acid sequence is dissimilar, suggesting that each protein may have diverged to perform different functions. It is also interesting to note that two regions at the amino terminus are conserved, even though the mature AKAP82 protein is processed to eliminate this portion of the protein (at a cleavage site depicted in the Figure). The third domain depicted in the Figure contains the putative RII binding site for both proteins; FIG. 5A provides a comparison, showing that 12 of the 18 amino acids of the binding site are conserved.

Despite the significant sequence homology between these two proteins, there is no cross-hybridization between cDNA encoding these proteins, and no cross-reactivity between either of these proteins and antibodies raised against the other. As described below, Northern blot analysis of germ cell-specific mRNA (or, as described above, screening a cDNA library prepared therefrom) using AKAP110 cDNA as a probe detected only AKAP mRNA or cDNA. Similarly, antibodies specific for AKAP110 detected only the single 110 kD AKAP110 protein band in Western blot experiments (described below). In addition, although AKAP82 has been reported to be an RII binding protein (see Carrera et al., ibid. and Visconti et al., ibid.), and the sequence comparison disclosed herein revealed significant sequence homology between the RII binding site of AKAP110 and the putative RII binding site of AKAP82, only AKAP110 was detected in RII overlay analyses of sperm protein extracts (as described in Example 1 and shown in FIG. 1). One explanation for these results is that AKAP110 has a higher affinity for RII that AKAP82, an explanation that is supported by the differences noted in the RII binding site. Importantly, the differences in RII binding suggests that the diversity at certain conserved positions in the RII binding site may be important: for example, AKAP82 has a valine at position 6 rather than an alanine or serine, and a serine at position 10 rather than a leucine, isoleucine, valine, alanine or threonine. These results suggest that these sites are particularly important for AKAP:RII interaction, which further suggests that these sites may be important targets for disrupting the AKAP:RII interaction in vivo, as described in greater detail below.

EXAMPLE 5

Expression of AKAP mRNA and Protein in Adult Tissues and in Sperm

AKAP110 expression in adult tissues was investigated at both the mRNA and protein levels.

In order to detect AKAP110 protein expression, polyclonal antisera were produced in rabbits. A peptide corresponding to amino acid residues 448–459 of bovine AKAP110 was synthesized using an automated peptide synthesizer and Fmoc chemistry (Applied Biosystems), having the following sequence:

SCVETLGEHIIK (Seq. ID No.: 1). This peptide was conjugated to keyhole limpet hemocyanin according to conventional protocols (Harlow & Lane, 1988, ANTIBODIES, Cold Spring Harbor Press: New York) and injected into two New Zealand white rabbits. The animals were bled from the ear after six weeks, the serum separated and then pooled. Ammonium sulfate was then added to the pooled serum to a final concentration of 40% to precipitate the immunoglobulin fraction. The precipitated antibodies were resuspended in phosphate buffered saline (PBS) and subjected to affinity chromatography using the original peptide (Seq ID No.: 1) conjugated to Amino Link matrix (obtained from Pierce Chemical Co.) according to the instructions from the supplier.

The plasmids prepared as described above in Example 2 were used to produce full-length AKAP110 in *E. coli* using ITPG induction as detailed in the instructions provided with the vector by the supplier (Novagen). The AKAP110 protein was then separated from other proteins by SDS/PAGE, and transferred to Immobilon P as described above. This Western blot was treated with BLOTTO solution (10 mM Tris-HCl (pH 7.5), 150 mM NaCl, 5% non-fat milk, 0.1% BSA) and then incubated with the primary antibody for two hours at room temperature using antibody dilutions of about 1:5000. Antibody binding was detected using antirabbit secondary antibody conjugated to horse radish peroxidase and developed using an enhanced chemiluminescence kit (Renaissance from NEN, Boston, Mass.) according to instructions from the supplier.

Figure 3:
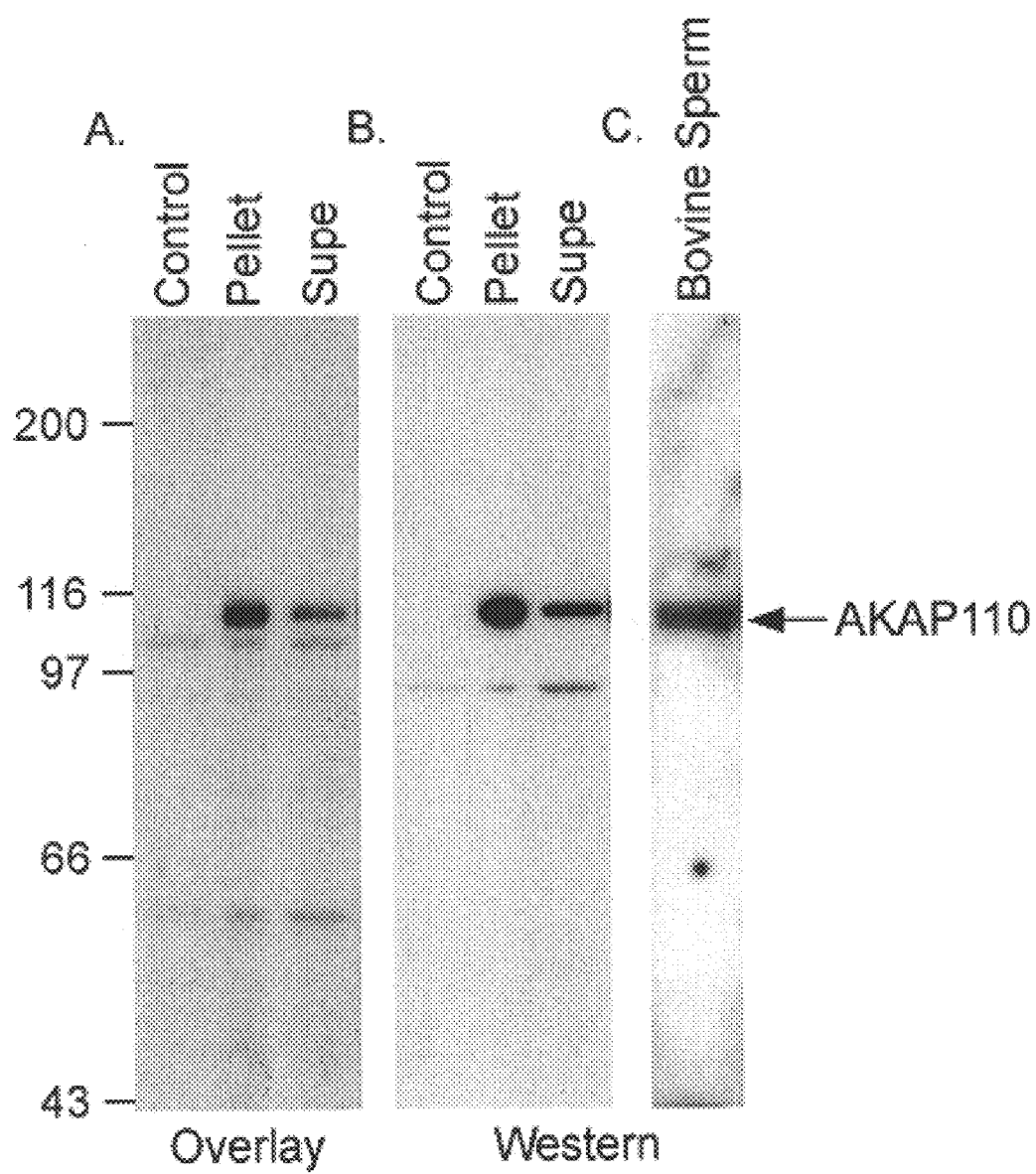
FIGS. 3A, 3B and 3C depict RII overlay (FIG. 3A) and Western blot assays (FIGS. 3B and 3C). Numbering in the left-hand side of FIG. 3A represents molecular weight markers (in kilodaltons).

Results of these experiments are shown in FIGS. 3A through 3C. FIGS. 3A and 3B are identical blots loaded with bacterial lysates from either uninduced (Control) or induced *E. coli*, and separated into pellet and supernatant fractions. FIG. 3A shows an RII overlay assay performed as described above, and confirms that intact, functional AKAP110 protein was produced and isolated from the *E. coli*. FIG. 3B is the result of probing this blot with the anti-AKAP110 antisera. These results show that the antisera specifically recognized the same protein band in the blot as the RII overlay assay. FIG. 3C shows a similar Western blot probed with the anti-AKAP110 antisera and containing 50 $\mu$g of bovine caudal sperm lysate (prepared as described in Example 1). These results demonstrate that the antisera were also capable of detecting native bovine AKAP110 in sperm protein lysates, and support the conclusion that the synthetic peptide raise antisera against native AKAP110.

Northern blots prepared using mouse polyA+mRNA from heart, brain, spleen, lung, liver, skeletal muscle, kidney and testis were obtained from Clontech; 2 $\mu$g of each tissue-specific mRNA were contained in each lane. These blots were hybridized according to the manufacturer's instructions with either full-length mouse AKAP110 cDNA or nucleotides 838–1055, labeled with a random hexamer primer kit (Amersham) to 1.5 million cpm/mL. The blot was thereafter washed sequentially using the following protocol: twice for 5 minutes apiece at room temperature in an excess volume of 2×SSC (0.03M sodium citrate dihydrate (pH 7.0), 0.3M NaCl), and 1% SDS; twice for 30 minutes apiece at room temperature in an excess volume of 0.2×SSC and 1% SDS; eight times at 46° C. in 0.1×SSC and 0.5% SDS. The blot was visualized by autoradiography by exposure to X-ray film (Kodak XAR, Eastman Kodak) overnight at −80° C.

Figure 7:
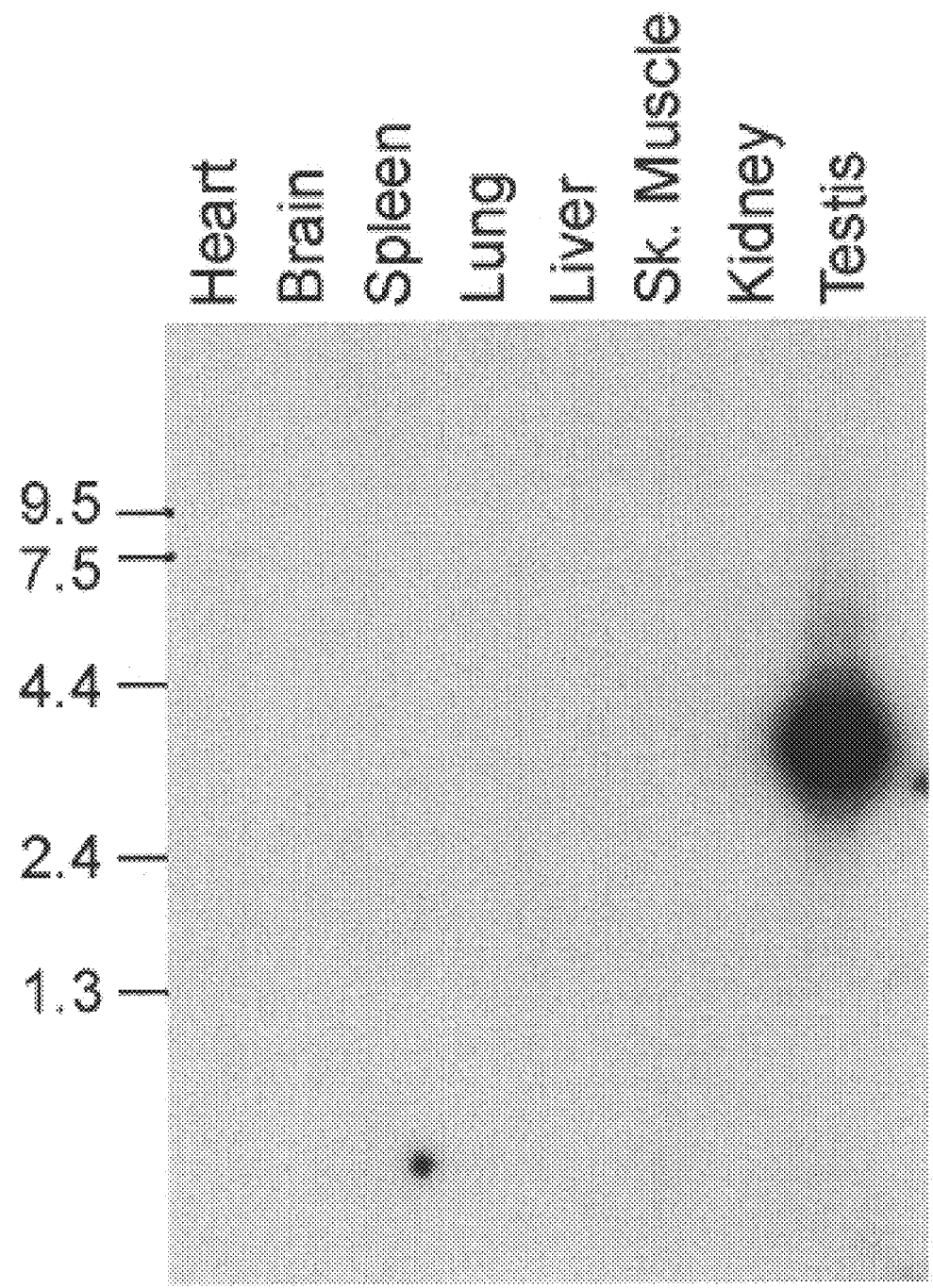
FIG. 7 is an autoradiogram of Northern blot hybridization of mRNAs from various mouse tissues probed with an AKAP 110 cDNA. Numbering in the left-hand side of the Figure represents molecular weight markers (in kilobases).

The results of these experiments are shown in FIG. 7. A single mouse AKAP110 mRNA of about 3.6 kb in size was detected specifically and only in mRNA from testis. These results indicate that AKAP110 expression may be sperm-specific. This conclusion is supported by the finding that all ESTs having similar sequences have been isolated only from testis cDNA libraries. The blots were probed with AKAP110 nucleotides 838–1055 to ensure that the detected mRNA was not the result of cross-hybridization with AKAP82 mRNA; this portion of the AKAP110 cDNA has no significant homology to the AKAP82 sequence. These results support the conclusion that, although the proteins are related, AKAP110 and AKAP82 cDNAs do not cross-hybridize.

In situ hybridization was performed on cryosections of fresh-frozen mouse testis tissue. Said cryosections were fixed in 4% formaldehyde in 0.1M Na-phosphate (pH 7.4), and then acetylated for 15 min in 0.25% acetic anhydride in 0.1M triethanolamine (pH 8). Sense and-antisense riboprobes were synthesized in the presence of digoxigenin-labeled nucleotides (Boehringer Mannheim, Indianapolis, Ind.) by run-off transcription of linearized pCRII plasmid (Invitrogen, San Diego, Calif.) containing a 217bp fragment of AKAP110 (residues 838–1055). Riboprobes were denatured for 5 min at 80° C., then diluted in 50% formamide, 10% dextran sulfate, 4×SSC, 1×Denhardt's reagent, 0.5mg/mL denatured salmon sperm DNA and 0.25mg/mL yeast tRNA. Frozen sections were hybridized at 50° C. overnight. After hybridization, slides were rinsed at room temperature with 2×SSC, rinsed again with STE (500 mM NaCl, 20 mM Tris-HCl (pH 7.5), 1mM EDTA), and then incubated for 30 min at 37° C. in STE containing 40 $\mu$g/mL RNase A. The slides were then washed twice for 5 min at room temperature, first in 1×SSC and then in 0.5×SSC. Hybridization was detected using sheep anti-digoxigenin Fab fragments conjugated with alkaline phosphatase (Boehringer Mannheim). Staining was achieved by incubation of the hybridized, antibody-bound sections with BCIP/NBT (bromo-4-chloro-3-indolphosphate/nitroblue tetrazolium, a substrate for alkaline phosphatase) in a solution of 100 mnM Tris-HCl (pH 9.5), 50 mM magnesium chloride, and 1 mM levamisole according to manufacturer's instructions.

Figure 8:
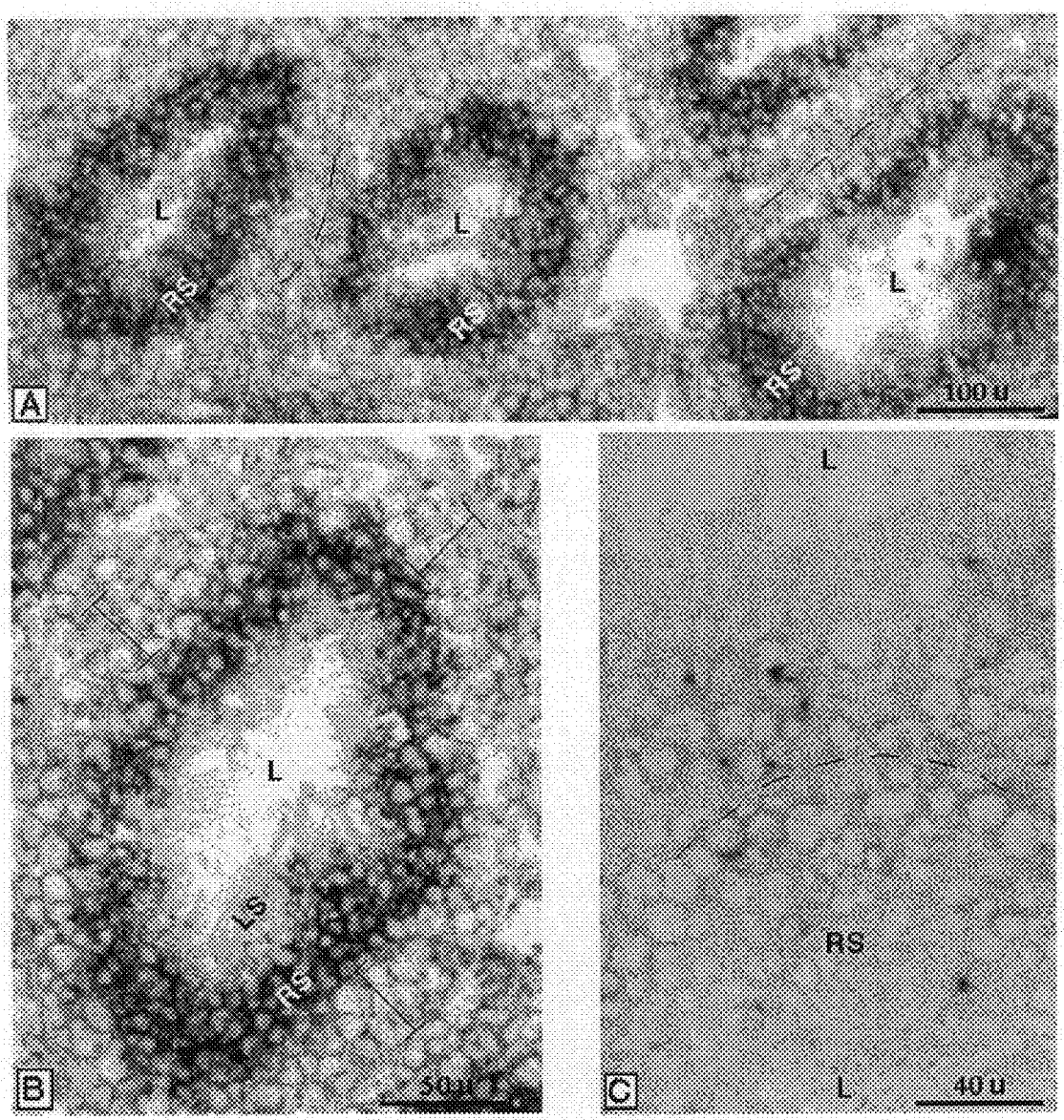
FIGS. 8A through 8C show the results of in situ hybridization analyses performed as described in Example 6.

The results of these assays are shown in FIGS. 8A and 8B. Antisense AKAP1110 riboprobe specifically hybridized to the seminiferous epithelium, and no hybridization was detected in either the interstitial tissue or in the peritubular and Sertoli cells of the seminiferous tubules, as shown in FIG. 8A produced by hybridization with the antisense probe. AKAP110 exhibited a stage-specific expression pattern in germ cells. No hybridization signal was detected in spermatogonia or spermatocytes, but expression was evident in round spermatids (FIG. 8B). FIG. 8C, which was hybridized with a sense-oriented probe showed no hybridization, as expected.

Figure 9B:
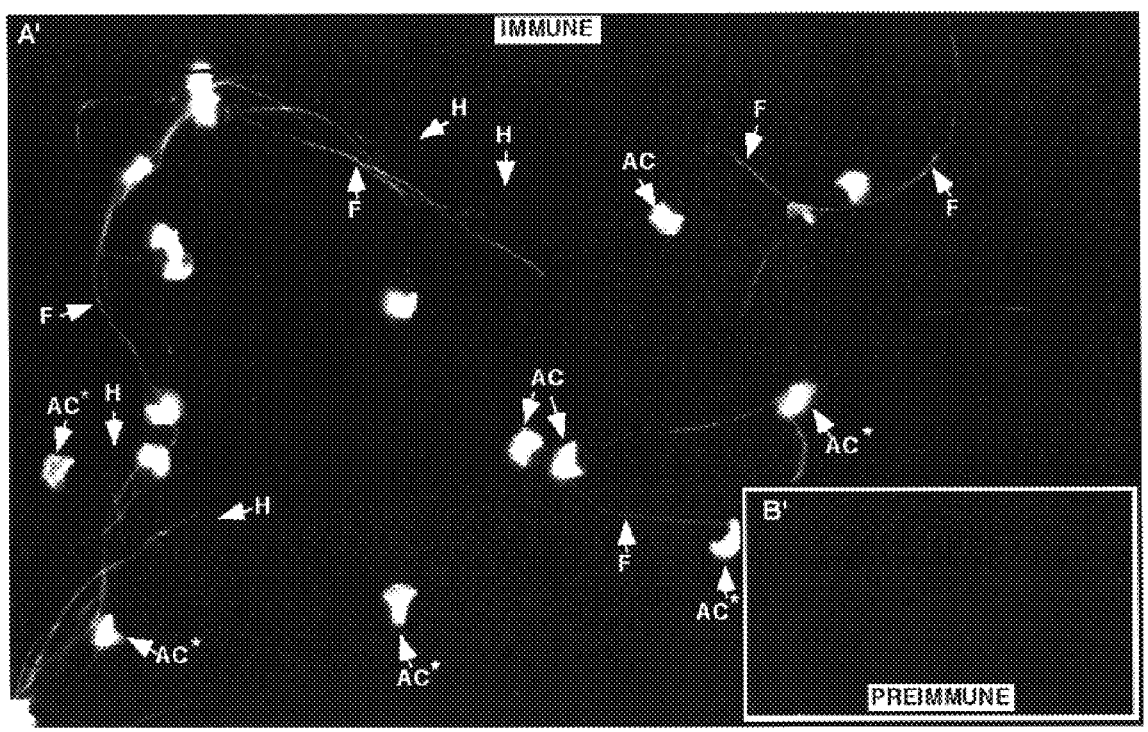

Intracellular localization of AKAP110 in sperm was determined by immunostaining. Ejaculated and epididymal caudal bovine sperm were collected by centrifugation at 1000×g for 10 min, then washed twice by resuspension in Hanks' saline or phosphate buffered saline (PBS) followed by centrifugation as above. Sperm were permeabilized either before or after fixation; no difference was found in the experimental results obtained. For permeabilizing sperm before fixation, the sperm were incubated at 4° C. for 30 min in a solution of 0.25% Triton X-100, 10 mm DTT, 150 mM NaCl, 25 mM Tris-HCl (pH 7.5), 2 mM benzamidine, 1 µg/mL leupeptin, and 14 µg/mL pepstatin, and then fixed in 4% formaldehyde in 0.1M sodium phosphate (pH 7.4). For permeabilizing sperm after fixation, sperm were fixed in 4% formaldehyde in 0.1M sodium phosphate (pH 7.4) at 4° C., then permeabilized for 30 min by the addition of Triton X-100 to a final concentration of 0.25%. Sperm were then attached to a poly-lysine coated coverglass which was then incubated in absolute acetone at 20° C. for 10 min and air-dried; alternatively, the coverglass was used directly for immunostaining Immunostaining was performed as follows. Sperm prepared as described above were rinsed in a solution of 10 mM Tris-HCl (pH 8.0), 150 mM NaCl, and 0.1% Tween 20 (termed "TNT solution"), then incubated for 1 h in a blocking solution of TNT containing 5% normal donkey serum and 2.5% BSA. In parallel, coverslips were incubated at least 1 h in equal dilutions of preimmune serum or anti-AKAP110 antisera diluted in blocking solution. After incubation, slides were rinsed three times in TNT containing 1% donkey serum; the slides were then incubated 1 h with cy3-conjugated, affinity-purified, donkey anti-rabbit IgG (obtained from Jackson ImmunoResearch Labs, West Grove, Pa.). The slide was then rinsed three times in TNT and observed by fluorescence and phase contrast microscopy; these results are shown in FIG. 9.

Ejaculated and caudal epididymal sperm exhibited identical specific staining patterns with anti-AKAP110 antisera, and no differences in staining were detected if the sperm were permeabilized before or after formaldehyde fixation. The flagellum and acrosomal regions were specifically stained with anti-AKAP110 antibody. Intense fluorescence was detected in the anterior acrosomal segment (shown in FIG. 9 and designated AC), but no staining was detected over the equatorial or post acrosomal segments of the head. Detached acrosomal caps also exhibited intense fluorescence (shown in FIG. 9 and designated AC*), and no fluorescence was detected on sperm heads after release of the acrosomal cap (shown in FIG. 9 and designated H). Specific fluorescence was detected over the full extent of the flagellum. No fluorescence staining was detected in matched sample incubated with preimmune serum (shown in FIG. 9 and designated B).

This pattern of AKAP110 localization is consistent with this protein being a dual AKAP, that is, being capable of binding to both the RI (found predominantly in sperm head) and RII (found predominantly in sperm flagellum) isoforms. The localization of AKAP in the acrosomal region of the sperm head suggests that disruption of this interaction may be a useful way of preventing fertilization.

EXAMPLE 6

Disruption of AKAP110/PKA Binding to Achieve Contraception in Adults

Isolation of mammalian AKAP110 cDNA as disclosed above enabled production of AKAP110 by recombinant genetic means. As described above, the cDNA inserts were cloned into an expression vector, pET30A, and introduced into E. coli cells. pET30A contains a Histidine tag sequence that was used to purify the fusion protein. Recombinant AKAP110 protein wasrecovered from said E. coli cells transformed with recombinant expression constructs comprising AKAP110-encoding cDNA.

The observation that disruption of AKAP : PKA binding inhibits sperm motility suggested that a high throughput in vitro screening system for detecting compounds that inhibit the AKAP : PKA interaction is useful for developing compounds useful as contraceptives. For example, a pharmaceutical compound directed at preventing or inhibiting sperm motility would provide for the first time a "male" contraceptive. This approach is particularly attractive, since Northern blot analysis of AKAP110 mRNA expression in a variety of tissues indicated that AKAP110 was specifically and exclusively expressed in male germ cells such as spermatogonia. Thus, any compound directed at specifically disrupting AKAP110: PKA binding has the potential for being used to develop a male contraceptive having minimal side effects on AKAP: PKA interactions in cell types other than sperm.

One embodiment of a high throughput analytical system comprises using a variant of the RII overlay assay described above to screen compounds for the capacity to prevent binding of a detectably-labeled RII protein. Recombinant RIIα is commercially available (Promega, Madison, Wis.), and can be detectably labeled with a radioactive, fluorescent or antigenic label. Alternatively, RII binding can be detected using RII-specific antibodies, which are also commercially available (Transduction Labs, Lexington, Ky.). Such assays are performed whereby the anti-RII antibodies are labeled directly, or in so-called "sandwich" assays using a labeled antibody specific for the anti-RII antibody (such as a using a labeled goat anti-rabbit antibody to detect rabbit polyclonal antisera as described above in Example 5). RII binding, and the disruption of RII binding in the presence of a test compound, can thereby be detected using either detectably-labeled recombinant RII or antibodies therefore, in binding assays using the recombinantly-produced AKAP110 proteins of the invention.

In alternative embodiments of these types of assays, recombinantly available AKAP110 or PKA is attached to a solid substrate, covalently or otherwise, and RII binding of said substrate is assayed analogous to either ELISA or radioimmune assay. In other embodiments, said solid substrate comprises materials such as chromatographic beads and other supports to which binding can be detected. These embodiments are particularly adapted for developing automated assays for screening a large number of compounds simultaneously. Also provided are competitive assays used to characterize binding affinities and inhibition constants of various binding inhibitors.

Alternatively, antisense oligonucleotides are used to inhibit, disrupt or prevent expression of AKAP110 in testis cells. An example of such an antisense oligonucleotide is one complementary to the sequence surrounding the initiation codon of AKAP110:

GCTTTGTAACCAGTCAACCTTTTCTGACAT (SEQ ID No. 18).

It should be understood that the foregoing disclosure emphasizes certain specific embodiments of the invention and that all modifications or alternatives equivalent thereto are within the spirit and scope of the invention as set forth in the appended claims.

We claim:

1. An isolated nucleic acid encoding a mammalian protein kinase A anchoring protein (AKAP) wherein said nucleic acid hybridizes to a nucleic acid probe identified by SEQ ID NOs: 10, 12, or 14 under high stringency conditions.

2. An isolated nucleic acid according to claim 1 encoding a mammalian protein AKAP having an amino acid sequence identified by SEQ ID NOs. 11, 13, or 15.

3. An isolated nucleic acid according to claim 2 encoding a human protein kinase A anchoring protein having the amino acid sequence identified by SEQ ID NO. 15.

4. An isolated nucleic acid according to claim 2 encoding a bovine protein kinase A anchoring protein having the amino acid sequence identified by SEQ ID NO. 13.

5. An isolated nucleic acid according to claim 2 encoding a murine protein kinase A anchoring protein having the amino acid sequence identified by SEQ ID NO. 11.

6. An isolated nucleic acid hybridization probe for a mammalian protein AKAP having an apparent molecular weight of about 110 kilodaltons as determined by denaturing SDS-PAGE comprising the nucleotide sequence identified by SEQ ID NO. 14.

7. An isolated nucleic acid hybridization probe for a mammalian protein AKAP having an apparent molecular weight of about 110 kilodaltons as determined by denaturing SDS-PAGE comprising the nucleotide sequence identified by SEQ ID NO. 12.

8. An isolated nucleic acid hybridization probe for a mammalian protein AKAP having an apparent molecular weight of about 110 kilodaltons as determined by denaturing SDS-PAGE comprising the nucleotide sequence identified by SEQ ID NO. 10.

9. An isolated recombinant expression construct comprising a nucleic acid having a nucleotide sequence encoding a mammalian protein AKAP having an apparent molecular weight of about 110 kilodaltons as determined by denaturing SDS-PAGE and having the amino acid sequence identified by SEQ ID NOs. 11, 13, 15, wherein said nucleic acid is operably linked to an expression control sequence.

10. A recombinant expression construct according to claim 9, wherein the nucleic acid encodes a human protein kinase A anchoring protein having the amino acid sequence identified by SEQ ID NO. 15.

11. A recombinant expression construct according to claim 9, wherein the nucleic acid encodes a bovine protein kinase A anchoring protein having the amino acid sequence identified by SEQ ID NO. 13.

12. A recombinant expression construct according to claim 9, wherein the nucleic acid encodes a murine protein kinase A anchoring protein having the amino acid sequence identified by SEQ ID NO. 11.

13. A host cell transformed with the recombinant expression construct of claim 9, wherein the transformed host cell expresses the mammalian protein AKAP.

14. A host cell transformed with the recombinant expression construct of claim 10, wherein the transformed host cell expresses the human protein AKAP.

15. A host cell transformed with the recombinant expression construct of claim 11, wherein the transformed host cell expresses the bovine protein AKAP.

16. A host cell transformed with the recombinant expression construct of claim 12, wherein the transformed host cell expresses the murine protein AKAP.

17. A method for preparing a recombinant nucleic acid encoding a mammalian protein AKAP having an apparent molecular weight of about 110 kilodaltons as determined by denaturing SDS-PAGE, the method comprising the steps of:

a) preparing or obtaining a recombinant DNA library from mammalian germ cell cDNA;

b) screening the library under high stringency conditions with a detectably labeled probe, wherein said probe is according to any one of claim 6, 7, or 8, and c) isolating positively-hybridizing clones, wherein said clones encode a mammalian protein AKAP.

18. The method of claim 17, wherein the detectably labeled probe is according to claim 6.

19. The method of claim 17, wherein the detectably labeled probe is according to claim 7.

20. The method of claim 17, wherein the detectably labeled probe is according to claim 8.

21. An antisense oligonucleotide that is SEQ ID NO: 18, wherein said antisense oligonucleotide can inhibit or reduce the expression of a mammalian protein AKAP having an apparent molecular weight of about 110 kilodaltons as determined by denaturing SDS-PAGE in testis cells, spermatids or progenitor cells thereof.

* * * * *

SEQUENCE LISTING

<160> NUMBER OF SEQ ID NOS: 33

<210> SEQ ID NO 1
<211> LENGTH: 12
<212> TYPE: PRT
<213> ORGANISM: Bos sp.
<220> FEATURE:
<223> OTHER INFORMATION: Description of Unknown Organism: cow

<400> SEQUENCE: 1

Ser Cys Val Glu Thr Leu Gly Glu His Ile Ile Lys
 1               5                  10

<210> SEQ ID NO 2
<211> LENGTH: 11
<212> TYPE: PRT
<213> ORGANISM: Bos sp.

<400> SEQUENCE: 2

Lys Gly Phe Cys Val Asp Tyr Tyr Asn Thr Thr
 1               5                  10

<210> SEQ ID NO 3
<211> LENGTH: 15
<212> TYPE: PRT
<213> ORGANISM: Bos sp.

<400> SEQUENCE: 3

Glu Gly Ile Ser Ala Cys Leu Gln Gly Ser Pro Phe Val Thr Pro
 1               5                  10                  15

<210> SEQ ID NO 4
<211> LENGTH: 11
<212> TYPE: PRT
<213> ORGANISM: Bos sp.

<400> SEQUENCE: 4

Ser Pro Ala Val Ser His Glu Ser Ser Leu Arg
 1               5                  10

<210> SEQ ID NO 5
<211> LENGTH: 9
<212> TYPE: PRT
<213> ORGANISM: Bos sp.

<400> SEQUENCE: 5

Asn Leu Leu Ser Glu Thr Ile Phe Lys
 1               5

<210> SEQ ID NO 6
<211> LENGTH: 20
<212> TYPE: PRT
<213> ORGANISM: Bos sp.

<400> SEQUENCE: 6

Gly Thr Gly Thr Ala Glu Thr Phe Leu Gln Asn Ala Tyr Gln Ala Ile
 1               5                  10                  15

His Asn Glu Leu
             20

<210> SEQ ID NO 7
<211> LENGTH: 11
<212> TYPE: PRT

<213> ORGANISM: Bos sp.

<400> SEQUENCE: 7

Leu Leu Gln Leu Ser Ala Ala Ala Val Glu Lys
 1               5                   10

<210> SEQ ID NO 8
<211> LENGTH: 432
<212> TYPE: DNA
<213> ORGANISM: Mus musculus

<400> SEQUENCE: 8

| | | | | | |
|---|---|---|---|---|---|
| atgagtgcaa | acttaagtct | cctccccaca | agatatgtga | ccaagaacaa | acagaaaaga | 60 |
| aagatctgat | gagtgtcatc | ttcaatttta | tccggaactt | actcagcgag | accatattca | 120 |
| agagtagccg | taactgtgaa | tccaatgtgc | atgagcagaa | cactcaggaa | gaagagatac | 180 |
| acccgtgtga | aaggcctaag | actccatgtg | aaaggcctat | taccccgcct | gccccgaaat | 240 |
| tctgtgagga | tgaggaggcc | actggtggtg | ccttatctgg | gctaaccaag | atggttgcca | 300 |
| accagctaga | caactgtatg | aatgggcaga | tggtggagca | cctgatggac | tcggtgatga | 360 |
| agttatgcct | cattattgcc | aagtcctgtg | actctcccct | gtcggagctg | ggagaggaaa | 420 |
| agtgtgggga | tg | | | | | 432 |

<210> SEQ ID NO 9
<211> LENGTH: 387
<212> TYPE: DNA
<213> ORGANISM: Homo sapiens

<400> SEQUENCE: 9

| | | | | | |
|---|---|---|---|---|---|
| gtgaatccaa | tgtgcatgag | cagaacactc | aggaagaaga | gatacacccg | tgtgaaaggc | 60 |
| ctaagactcc | atgtgaaagg | cctattaccc | cgcctgcccc | gaaattctgt | gaggatgagg | 120 |
| aggccactgg | tggtgcctta | tctgggctaa | ccaagatggt | tgccaaccag | ctagacaact | 180 |
| gtatgaatgg | gcagatggtg | gagcacctga | tggactcggt | gatgaagtta | tgcctcatta | 240 |
| ttgccaagtc | ctgtgactct | cccctgtcgg | agctgggaga | ggaaaagtgt | ggggatgcca | 300 |
| gccggccaaa | ttctgccttc | ccagataact | tatatgagtg | cctaccagtc | aagggcacag | 360 |
| ggacagctga | agccctcctg | cagaacg | | | | 387 |

<210> SEQ ID NO 10
<211> LENGTH: 3103
<212> TYPE: DNA
<213> ORGANISM: Mus musculus
<220> FEATURE:
<221> NAME/KEY: 5'UTR
<222> LOCATION: (1)..(291)
<220> FEATURE:
<221> NAME/KEY: CDS
<222> LOCATION: (292)..(2883)
<220> FEATURE:
<221> NAME/KEY: 3'UTR
<222> LOCATION: (2884)..(3078)

<400> SEQUENCE: 10

| | | | | | |
|---|---|---|---|---|---|
| agaacatccc | agcatcttca | ttgactttaa | aagtatattc | tggagtcttc | tgtggttccc | 60 |
| tataacagag | cttcagaggt | tctccgattt | taagaaagat | gagctgcctg | gaattacaaa | 120 |
| tgggcaggac | ttttctattc | actctttcaa | caggaaaatt | actaagcacc | aacgttaaag | 180 |
| agtccttata | tattacatgg | caggaggggt | gggtagactt | agggatagtg | aagacaccaa | 240 |
| taaggctcat | tcggagtctt | ccttgtatct | caaaacccat | cctcaataag | g atg gcg | 297 |

```
                                                        Met Ala
                                                         1
gat agg gtt gac tgg tta caa agt caa agt ggc gtt tgc aaa gtt ggt      345
Asp Arg Val Asp Trp Leu Gln Ser Gln Ser Gly Val Cys Lys Val Gly
         5                  10                 15 gtc tat tca cct gga gac aac caa cac caa gac tgg aaa atg gac aca      393
Val Tyr Ser Pro Gly Asp Asn Gln His Gln Asp Trp Lys Met Asp Thr
     20                  25                  30 tca aca gat cct gtc cga gtg ctc agc tgg ctc cgc aaa gac ctg gag      441
Ser Thr Asp Pro Val Arg Val Leu Ser Trp Leu Arg Lys Asp Leu Glu
 35              40                  45                  50 aaa agt aca gcg ggc ttc cag gac tcg agg ttc aag cct gga gag tca      489
Lys Ser Thr Ala Gly Phe Gln Asp Ser Arg Phe Lys Pro Gly Glu Ser
                 55                  60                  65 tcg ttt gtg gag gaa gtg gct tac cca gtg gac caa cga aaa ggt ttc      537
Ser Phe Val Glu Glu Val Ala Tyr Pro Val Asp Gln Arg Lys Gly Phe
             70                  75                  80 tgt gtt gat tat tac aat acc acc aac aag ggc agt cca gga aga ttg      585
Cys Val Asp Tyr Tyr Asn Thr Thr Asn Lys Gly Ser Pro Gly Arg Leu
         85                  90                  95 cat ttt gag atg tct cac aag gag aac cct tcc cag ggc ctc att tcc      633
His Phe Glu Met Ser His Lys Glu Asn Pro Ser Gln Gly Leu Ile Ser
    100                 105                 110 cat gtt ggt aat ggg ggt tcc ata gac gaa gtt tcc ttc tat gcc aac      681
His Val Gly Asn Gly Gly Ser Ile Asp Glu Val Ser Phe Tyr Ala Asn
115                 120                 125                 130 cgc ctc aca aac cta gtg atc gcc atg gcc cga aag gag atc aat gag      729
Arg Leu Thr Asn Leu Val Ile Ala Met Ala Arg Lys Glu Ile Asn Glu
                135                 140                 145 aag atc cac ggc gct gaa aac aaa tgt gtc cat cag tca ttg tat atg      777
Lys Ile His Gly Ala Glu Asn Lys Cys Val His Gln Ser Leu Tyr Met
            150                 155                 160 ggg gat gag ccc aca ccc cac aaa agc ttg agt aca gtg gcc tct gag      825
Gly Asp Glu Pro Thr Pro His Lys Ser Leu Ser Thr Val Ala Ser Glu
        165                 170                 175 ctc gtg aac gag aca gtc acc gca tgt tcc aag aac att tcc agt gac      873
Leu Val Asn Glu Thr Val Thr Ala Cys Ser Lys Asn Ile Ser Ser Asp
    180                 185                 190 aaa gct ccc ggc tct gga gac agg gcc tcg ggg tcg tca cag gcc cct      921
Lys Ala Pro Gly Ser Gly Asp Arg Ala Ser Gly Ser Ser Gln Ala Pro
195                 200                 205                 210 ggt cta aga tac atg agc act ctg aag atc aag gag agt aca aag gaa      969
Gly Leu Arg Tyr Met Ser Thr Leu Lys Ile Lys Glu Ser Thr Lys Glu
                215                 220                 225 ggc aag tgt cca gac gac aag ccc ggc act aag aag tct ttc ttc tat     1017
Gly Lys Cys Pro Asp Asp Lys Pro Gly Thr Lys Lys Ser Phe Phe Tyr
            230                 235                 240 aag gaa gtg ttt gag tcc cgg aat gca gga gat gcc aag gag ggc ggg     1065
Lys Glu Val Phe Glu Ser Arg Asn Ala Gly Asp Ala Lys Glu Gly Gly
        245                 250                 255 agg tcc tta ccc gga gat caa aaa ctg ttc agg acc agc ccc gac aac     1113
Arg Ser Leu Pro Gly Asp Gln Lys Leu Phe Arg Thr Ser Pro Asp Asn
    260                 265                 270 agg cct gat gac ttt tca aac tct atc agt caa ggg atc atg acc tac     1161
Arg Pro Asp Asp Phe Ser Asn Ser Ile Ser Gln Gly Ile Met Thr Tyr
275                 280                 285                 290 gcc aac agc gtg gtg tct gac atg atg gtc tcc atc atg aag acg ctg     1209
Ala Asn Ser Val Val Ser Asp Met Met Val Ser Ile Met Lys Thr Leu
                295                 300                 305
```

```
aag atc cag gtg aag gac aca acc atc gcc acg att ctg ctg aag aag    1257
Lys Ile Gln Val Lys Asp Thr Thr Ile Ala Thr Ile Leu Leu Lys Lys
        310                 315                 320 gtg ctg atg aag cat gca aag gag gtt gtc tcc gac ctc atc gac tcc    1305
Val Leu Met Lys His Ala Lys Glu Val Val Ser Asp Leu Ile Asp Ser
325                 330                 335 ttc atg aag aac ctc cac ggc gtc acg gga agc ctc atg act gac aca    1353
Phe Met Lys Asn Leu His Gly Val Thr Gly Ser Leu Met Thr Asp Thr
        340                 345                 350 gac ttt gtc tcg gcc gtg aaa cga agt ttt ttt tct cat gga agc caa    1401
Asp Phe Val Ser Ala Val Lys Arg Ser Phe Phe Ser His Gly Ser Gln
355                 360                 365                 370 aag gcc aca gat atc atg gat gcc atg ctg ggc aag cta tac aat gtg    1449
Lys Ala Thr Asp Ile Met Asp Ala Met Leu Gly Lys Leu Tyr Asn Val
            375                 380                 385 atg ttt gcc aag aaa ttc cct gag aac atc cgg aga gcc agg gac aag    1497
Met Phe Ala Lys Lys Phe Pro Glu Asn Ile Arg Arg Ala Arg Asp Lys
        390                 395                 400 tcg gag agt tac tcc ctt atc tcc acg aaa tca cgg gct ggt gac cca    1545
Ser Glu Ser Tyr Ser Leu Ile Ser Thr Lys Ser Arg Ala Gly Asp Pro
            405                 410                 415 aag ctc tca aat ttg aac ttt gcg atg aag tca gaa tca aag ctg aaa    1593
Lys Leu Ser Asn Leu Asn Phe Ala Met Lys Ser Glu Ser Lys Leu Lys
        420                 425                 430 gaa aat ttg ttt tct aca tgc aaa cta gag aaa gag aag acg tgt gcc    1641
Glu Asn Leu Phe Ser Thr Cys Lys Leu Glu Lys Glu Lys Thr Cys Ala
435                 440                 445                 450 gaa act ctg ggt gag cat att att aag gag gga ctg cac atg tgg cac    1689
Glu Thr Leu Gly Glu His Ile Ile Lys Glu Gly Leu His Met Trp His
                455                 460                 465 aag agt cag caa aaa tct cct ggc ttg gag cgt gcc gca aaa ctg ggt    1737
Lys Ser Gln Gln Lys Ser Pro Gly Leu Glu Arg Ala Ala Lys Leu Gly
        470                 475                 480 aac gct cca cag gag gtc tcc ttt gag tgc cca gat cct tgt gag gca    1785
Asn Ala Pro Gln Glu Val Ser Phe Glu Cys Pro Asp Pro Cys Glu Ala
            485                 490                 495 aac cct cct cac caa cct cag cca cca gag aat ttt gca aat ttt atg    1833
Asn Pro Pro His Gln Pro Gln Pro Pro Glu Asn Phe Ala Asn Phe Met
500                 505                 510 tgt gac tca gac tcc tgg gcc aag gac ctg att gta tct gcc ctg ctt    1881
Cys Asp Ser Asp Ser Trp Ala Lys Asp Leu Ile Val Ser Ala Leu Leu
515                 520                 525                 530 ctg att cag tat cac ctg gca cag gga gga aag atg gat gct cag agc    1929
Leu Ile Gln Tyr His Leu Ala Gln Gly Gly Lys Met Asp Ala Gln Ser
                535                 540                 545 ttc ctg gaa gct gct gcc agc acc aat ttt ccc acc aac aag cca cct    1977
Phe Leu Glu Ala Ala Ala Ser Thr Asn Phe Pro Thr Asn Lys Pro Pro
        550                 555                 560 cct cct tct cct gta gtt cag gat gag tgc aaa ctt aag tct cct ccc    2025
Pro Pro Ser Pro Val Val Gln Asp Glu Cys Lys Leu Lys Ser Pro Pro
            565                 570                 575 cac aag ata tgt gac caa gaa caa aca gaa aag aaa gat ctg atg agt    2073
His Lys Ile Cys Asp Gln Glu Gln Thr Glu Lys Lys Asp Leu Met Ser
580                 585                 590 gtc atc ttc aat ttt atc cgg aac tta ctc agc gag acc ata ttc aag    2121
Val Ile Phe Asn Phe Ile Arg Asn Leu Leu Ser Glu Thr Ile Phe Lys
595                 600                 605                 610 agt agc cgt aac tgt gaa tcc aat gtg cat gag cag aac act cag gaa    2169
Ser Ser Arg Asn Cys Glu Ser Asn Val His Glu Gln Asn Thr Gln Glu
                615                 620                 625
```

-continued

```
gaa gag ata cac ccg tgt gaa agg cct aag act cca tgt gaa agg cct      2217
Glu Glu Ile His Pro Cys Glu Arg Pro Lys Thr Pro Cys Glu Arg Pro
            630                 635                 640 att acc ccg cct gcc ccg aaa ttc tgt gag gat gag gag gcc act ggt      2265
Ile Thr Pro Pro Ala Pro Lys Phe Cys Glu Asp Glu Glu Ala Thr Gly
            645                 650                 655 ggt gcc tta tct ggg cta acc aag atg gtt gcc aac cag cta gac aac      2313
Gly Ala Leu Ser Gly Leu Thr Lys Met Val Ala Asn Gln Leu Asp Asn
        660                 665                 670 tgt atg aat ggg cag atg gtg gag cac ctg atg gac tcg gtg atg aag      2361
Cys Met Asn Gly Gln Met Val Glu His Leu Met Asp Ser Val Met Lys
675                 680                 685                 690 tta tgc ctc att att gcc aag tcc tgt gac tct ccc ctg tcg gag ctg      2409
Leu Cys Leu Ile Ile Ala Lys Ser Cys Asp Ser Pro Leu Ser Glu Leu
                695                 700                 705 gga gag gaa aag tgt ggg gat gcc agc cgg cca aat tct gcc ttc cca      2457
Gly Glu Glu Lys Cys Gly Asp Ala Ser Arg Pro Asn Ser Ala Phe Pro
            710                 715                 720 gat aac tta tat gag tgc cta cca gtc aag ggc aca ggg aca gct gaa      2505
Asp Asn Leu Tyr Glu Cys Leu Pro Val Lys Gly Thr Gly Thr Ala Glu
            725                 730                 735 gcc ctc ctg cag aac gcc tac ctc acc atc cat aat gaa ctg aga ggt      2553
Ala Leu Leu Gln Asn Ala Tyr Leu Thr Ile His Asn Glu Leu Arg Gly
        740                 745                 750 ttg tca gga cag ccc ccc gag ggc tgt gaa atc ccc aag gtg atc gtc      2601
Leu Ser Gly Gln Pro Pro Glu Gly Cys Glu Ile Pro Lys Val Ile Val
755                 760                 765                 770 agc aac cac aat ctg gct gac acc gtt cag aac aag caa ctg caa gct      2649
Ser Asn His Asn Leu Ala Asp Thr Val Gln Asn Lys Gln Leu Gln Ala
                775                 780                 785 gtc ctt cag tgg gtg gct gcc tca gag ctc aat gtc cct att ttg tac      2697
Val Leu Gln Trp Val Ala Ala Ser Glu Leu Asn Val Pro Ile Leu Tyr
            790                 795                 800 ttt gct ggt gac gat gaa gga atc cag gag aag ctg ctt cag ctc tca      2745
Phe Ala Gly Asp Asp Glu Gly Ile Gln Glu Lys Leu Leu Gln Leu Ser
            805                 810                 815 gcc act gcc gtg gag aaa ggc cgc agc gtt ggg gag gtt ctg cag tcg      2793
Ala Thr Ala Val Glu Lys Gly Arg Ser Val Gly Glu Val Leu Gln Ser
        820                 825                 830 gtg ctg agg tac gag aag gag cga cag ctg gat gaa gca gtg gga aat      2841
Val Leu Arg Tyr Glu Lys Glu Arg Gln Leu Asp Glu Ala Val Gly Asn
835                 840                 845                 850 gtc acg cgg ctg cag ctg ctg gac tgg ctg atg gca aac ctg              2883
Val Thr Arg Leu Gln Leu Leu Asp Trp Leu Met Ala Asn Leu
                855                 860 tgattggggc ctaccctgag ttccctcagc gggccgagtc cccgcccctc cagccccctc    2943
catgccccac agagccctaa agtcccctcc atgccaccca cactaaacac gccatctaac    3003
gctactcact ggattttgca gattttcttg tccatgcgag caaggacata aatgaaaga     3063 ttacagttaa agggcaaaaa aaaaaaaaaa aaaaaaaaa                           3103
```

<210> SEQ ID NO 11
<211> LENGTH: 864
<212> TYPE: PRT
<213> ORGANISM: Mus musculus

<400> SEQUENCE: 11

```
Met Ala Asp Arg Val Asp Trp Leu Gln Ser Gln Ser Gly Val Cys Lys
 1               5                   10                  15
```

-continued

```
Val Gly Val Tyr Ser Pro Gly Asp Asn Gln His Gln Asp Trp Lys Met
             20                  25                  30

Asp Thr Ser Thr Asp Pro Val Arg Val Leu Ser Trp Leu Arg Lys Asp
         35                  40                  45

Leu Glu Lys Ser Thr Ala Gly Phe Gln Asp Ser Arg Phe Lys Pro Gly
     50                  55                  60

Glu Ser Ser Phe Val Glu Val Ala Tyr Pro Val Asp Gln Arg Lys
 65                  70                  75                  80

Gly Phe Cys Val Asp Tyr Tyr Asn Thr Thr Asn Lys Gly Ser Pro Gly
                 85                  90                  95

Arg Leu His Phe Glu Met Ser His Lys Glu Asn Pro Ser Gln Gly Leu
             100                 105                 110

Ile Ser His Val Gly Asn Gly Gly Ser Ile Asp Glu Val Ser Phe Tyr
         115                 120                 125

Ala Asn Arg Leu Thr Asn Leu Val Ile Ala Met Ala Arg Lys Glu Ile
     130                 135                 140

Asn Glu Lys Ile His Gly Ala Glu Asn Lys Cys Val His Gln Ser Leu
145                 150                 155                 160

Tyr Met Gly Asp Glu Pro Thr Pro His Lys Ser Leu Ser Thr Val Ala
                 165                 170                 175

Ser Glu Leu Val Asn Glu Thr Val Thr Ala Cys Ser Lys Asn Ile Ser
             180                 185                 190

Ser Asp Lys Ala Pro Gly Ser Gly Asp Arg Ala Ser Gly Ser Ser Gln
         195                 200                 205

Ala Pro Gly Leu Arg Tyr Met Ser Thr Leu Lys Ile Lys Glu Ser Thr
     210                 215                 220

Lys Glu Gly Lys Cys Pro Asp Asp Lys Pro Gly Thr Lys Lys Ser Phe
225                 230                 235                 240

Phe Tyr Lys Glu Val Phe Glu Ser Arg Asn Ala Gly Asp Ala Lys Glu
                 245                 250                 255

Gly Gly Arg Ser Leu Pro Gly Asp Gln Lys Leu Phe Arg Thr Ser Pro
             260                 265                 270

Asp Asn Arg Pro Asp Asp Phe Ser Asn Ser Ile Ser Gln Gly Ile Met
         275                 280                 285

Thr Tyr Ala Asn Ser Val Val Ser Asp Met Met Val Ser Ile Met Lys
     290                 295                 300

Thr Leu Lys Ile Gln Val Lys Asp Thr Thr Ile Ala Thr Ile Leu Leu
305                 310                 315                 320

Lys Lys Val Leu Met Lys His Ala Lys Glu Val Val Ser Asp Leu Ile
                 325                 330                 335

Asp Ser Phe Met Lys Asn Leu His Gly Val Thr Gly Ser Leu Met Thr
             340                 345                 350

Asp Thr Asp Phe Val Ser Ala Val Lys Arg Ser Phe Phe Ser His Gly
         355                 360                 365

Ser Gln Lys Ala Thr Asp Ile Met Asp Ala Met Leu Gly Lys Leu Tyr
     370                 375                 380

Asn Val Met Phe Ala Lys Lys Phe Pro Glu Asn Ile Arg Arg Ala Arg
385                 390                 395                 400

Asp Lys Ser Glu Ser Tyr Ser Leu Ile Ser Thr Lys Ser Arg Ala Gly
                 405                 410                 415

Asp Pro Lys Leu Ser Asn Leu Asn Phe Ala Met Lys Ser Glu Ser Lys
             420                 425                 430
```

-continued

```
Leu Lys Glu Asn Leu Phe Ser Thr Cys Lys Leu Glu Lys Glu Lys Thr
        435                 440                 445
Cys Ala Glu Thr Leu Gly Glu His Ile Ile Lys Glu Gly Leu His Met
        450                 455                 460
Trp His Lys Ser Gln Gln Lys Ser Pro Gly Leu Glu Arg Ala Ala Lys
465                 470                 475                 480
Leu Gly Asn Ala Pro Gln Glu Val Ser Phe Glu Cys Pro Asp Pro Cys
                485                 490                 495
Glu Ala Asn Pro Pro His Gln Pro Gln Pro Glu Asn Phe Ala Asn
                500                 505                 510
Phe Met Cys Asp Ser Asp Ser Trp Ala Lys Asp Leu Ile Val Ser Ala
        515                 520                 525
Leu Leu Leu Ile Gln Tyr His Leu Ala Gln Gly Gly Lys Met Asp Ala
        530                 535                 540
Gln Ser Phe Leu Glu Ala Ala Ser Thr Asn Phe Pro Thr Asn Lys
545                 550                 555                 560
Pro Pro Pro Pro Ser Pro Val Val Gln Asp Glu Cys Lys Leu Lys Ser
                565                 570                 575
Pro Pro His Lys Ile Cys Asp Gln Glu Gln Thr Glu Lys Lys Asp Leu
                580                 585                 590
Met Ser Val Ile Phe Asn Phe Ile Arg Asn Leu Leu Ser Glu Thr Ile
        595                 600                 605
Phe Lys Ser Ser Arg Asn Cys Glu Ser Asn Val His Glu Gln Asn Thr
        610                 615                 620
Gln Glu Glu Glu Ile His Pro Cys Glu Arg Pro Lys Thr Pro Cys Glu
625                 630                 635                 640
Arg Pro Ile Thr Pro Pro Ala Pro Lys Phe Cys Glu Asp Glu Glu Ala
                645                 650                 655
Thr Gly Gly Ala Leu Ser Gly Leu Thr Lys Met Val Ala Asn Gln Leu
                660                 665                 670
Asp Asn Cys Met Asn Gly Gln Met Val Glu His Leu Met Asp Ser Val
        675                 680                 685
Met Lys Leu Cys Leu Ile Ile Ala Lys Ser Cys Asp Ser Pro Leu Ser
        690                 695                 700
Glu Leu Gly Glu Glu Lys Cys Gly Asp Ala Ser Arg Pro Asn Ser Ala
705                 710                 715                 720
Phe Pro Asp Asn Leu Tyr Glu Cys Leu Pro Val Lys Gly Thr Gly Thr
                725                 730                 735
Ala Glu Ala Leu Leu Gln Asn Ala Tyr Leu Thr Ile His Asn Glu Leu
                740                 745                 750
Arg Gly Leu Ser Gly Gln Pro Pro Glu Gly Cys Glu Ile Pro Lys Val
        755                 760                 765
Ile Val Ser Asn His Asn Leu Ala Asp Thr Val Gln Asn Lys Gln Leu
        770                 775                 780
Gln Ala Val Leu Gln Trp Val Ala Ala Ser Glu Leu Asn Val Pro Ile
785                 790                 795                 800
Leu Tyr Phe Ala Gly Asp Asp Glu Gly Ile Gln Glu Lys Leu Leu Gln
                805                 810                 815
Leu Ser Ala Thr Ala Val Glu Lys Gly Arg Ser Val Gly Glu Val Leu
                820                 825                 830
Gln Ser Val Leu Arg Tyr Glu Lys Glu Arg Gln Leu Asp Glu Ala Val
        835                 840                 845
Gly Asn Val Thr Arg Leu Gln Leu Leu Asp Trp Leu Met Ala Asn Leu
```

<210> SEQ ID NO 12
<211> LENGTH: 2562
<212> TYPE: DNA
<213> ORGANISM: Bos sp.
<220> FEATURE:
<221> NAME/KEY: CDS
<222> LOCATION: (1)..(2562)

<400> SEQUENCE: 12

| | | | | | | | | | | | | | | | | |
|---|---|---|---|---|---|---|---|---|---|---|---|---|---|---|---|---|
| gtt | gac | tgg | tta | caa | agc | caa | aat | gga | gta | tgc | aaa | gtt | gac | gtc | tat | 48 |
| Val | Asp | Trp | Leu | Gln | Ser | Gln | Asn | Gly | Val | Cys | Lys | Val | Asp | Val | Tyr | |
| 1 | | | | 5 | | | | | 10 | | | | | 15 | | |
| tcc | ccc | gga | gac | agc | caa | ccc | caa | gac | tgg | aaa | atg | tcg | gat | gaa | tcc | 96 |
| Ser | Pro | Gly | Asp | Ser | Gln | Pro | Gln | Asp | Trp | Lys | Met | Ser | Asp | Glu | Ser | |
| | | | 20 | | | | | 25 | | | | | 30 | | | |
| ttg | tct | att | ttt | aag | gaa | gcc | tca | cac | gat | ccc | atc | aga | gtg | ctc | agc | 144 |
| Leu | Ser | Ile | Phe | Lys | Glu | Ala | Ser | His | Asp | Pro | Ile | Arg | Val | Leu | Ser | |
| | | | 35 | | | | | 40 | | | | | 45 | | | |
| tgg | ctc | cgc | aga | gac | ctg | gaa | aaa | agc | aca | gca | gga | ttc | caa | gac | att | 192 |
| Trp | Leu | Arg | Arg | Asp | Leu | Glu | Lys | Ser | Thr | Ala | Gly | Phe | Gln | Asp | Ile | |
| | 50 | | | | | 55 | | | | | 60 | | | | | |
| agg | ttc | aag | ccc | gga | gaa | tca | tcg | ctc | ggc | agg | gaa | atg | gtc | agc | tca | 240 |
| Arg | Phe | Lys | Pro | Gly | Glu | Ser | Ser | Leu | Gly | Arg | Glu | Met | Val | Ser | Ser | |
| 65 | | | | | 70 | | | | | 75 | | | | | 80 | |
| gga | gac | cca | cgc | aaa | ggt | ttc | tgc | gtg | gac | tat | tac | aac | acc | acc | tcc | 288 |
| Gly | Asp | Pro | Arg | Lys | Gly | Phe | Cys | Val | Asp | Tyr | Tyr | Asn | Thr | Thr | Ser | |
| | | | | 85 | | | | | 90 | | | | | 95 | | |
| agg | gga | agt | cca | ggg | agg | ctg | cat | ttt | gag | atg | agt | cac | aga | gag | aac | 336 |
| Arg | Gly | Ser | Pro | Gly | Arg | Leu | His | Phe | Glu | Met | Ser | His | Arg | Glu | Asn | |
| | | | 100 | | | | | 105 | | | | | 110 | | | |
| cca | cac | cag | ggc | ccc | acc | tgc | aat | ggg | agc | tcc | gta | gat | gaa | gtc | tcc | 384 |
| Pro | His | Gln | Gly | Pro | Thr | Cys | Asn | Gly | Ser | Ser | Val | Asp | Glu | Val | Ser | |
| | | 115 | | | | | 120 | | | | | 125 | | | | |
| ttc | tac | gcc | aac | cgc | ctc | aca | aat | ctt | gtc | atc | gcc | atg | gcc | cgc | aag | 432 |
| Phe | Tyr | Ala | Asn | Arg | Leu | Thr | Asn | Leu | Val | Ile | Ala | Met | Ala | Arg | Lys | |
| | | 130 | | | | | 135 | | | | | 140 | | | | |
| gag | atc | aac | gag | aag | att | gac | ggc | tct | gaa | aac | agg | tgt | gtc | cac | caa | 480 |
| Glu | Ile | Asn | Glu | Lys | Ile | Asp | Gly | Ser | Glu | Asn | Arg | Cys | Val | His | Gln | |
| 145 | | | | | 150 | | | | | 155 | | | | | 160 | |
| tca | gtg | tac | atg | ggg | gat | gag | cct | cca | ccc | aac | aag | agc | ctg | agc | aag | 528 |
| Ser | Val | Tyr | Met | Gly | Asp | Glu | Pro | Pro | Pro | Asn | Lys | Ser | Leu | Ser | Lys | |
| | | | | 165 | | | | | 170 | | | | | 175 | | |
| gtg | gcg | tcg | gag | ctg | gtg | aat | gag | acc | gtc | act | gcc | tgc | tcc | aaa | aac | 576 |
| Val | Ala | Ser | Glu | Leu | Val | Asn | Glu | Thr | Val | Thr | Ala | Cys | Ser | Lys | Asn | |
| | | | 180 | | | | | 185 | | | | | 190 | | | |
| acc | cca | tca | gat | aag | gct | ccg | ggc | tct | ggt | gac | aga | gcc | tcg | ggg | aca | 624 |
| Thr | Pro | Ser | Asp | Lys | Ala | Pro | Gly | Ser | Gly | Asp | Arg | Ala | Ser | Gly | Thr | |
| | | 195 | | | | | 200 | | | | | 205 | | | | |
| tta | cag | agc | ccc | cca | aat | tta | aaa | tac | aaa | agc | act | ttg | aag | atc | aag | 672 |
| Leu | Gln | Ser | Pro | Pro | Asn | Leu | Lys | Tyr | Lys | Ser | Thr | Leu | Lys | Ile | Lys | |
| | 210 | | | | | 215 | | | | | 220 | | | | | |
| gaa | agc | aac | aag | gga | ggc | agg | ggt | cca | gac | gac | agg | cct | agc | tct | aag | 720 |
| Glu | Ser | Asn | Lys | Gly | Gly | Arg | Gly | Pro | Asp | Asp | Arg | Pro | Ser | Ser | Lys | |
| 225 | | | | | 230 | | | | | 235 | | | | | 240 | |
| aag | tct | ctc | ttc | tac | aag | gaa | gta | ttc | gaa | tct | cgt | aac | gcg | ggt | gat | 768 |
| Lys | Ser | Leu | Phe | Tyr | Lys | Glu | Val | Phe | Glu | Ser | Arg | Asn | Ala | Gly | Asp | |
| | | | | 245 | | | | | 250 | | | | | 255 | | |
| gcc | aaa | gag | gga | gga | agg | acc | tta | ccg | gcg | gag | aga | aag | atg | ttc | aga | 816 |
| Ala | Lys | Glu | Gly | Gly | Arg | Thr | Leu | Pro | Ala | Glu | Arg | Lys | Met | Phe | Arg | |

-continued

| | | | | | | | | | | | | | | | | |
|---|---|---|---|---|---|---|---|---|---|---|---|---|---|---|---|---|
| | | 260 | | | | | 265 | | | | | 270 | | | | |
| ggg | tat | gaa | agg | ccc | gat | gac | ttc | aca | gct | tcc | atc | agt | caa | ggg | atc | 864 |
| Gly | Tyr | Glu | Arg | Pro | Asp | Asp | Phe | Thr | Ala | Ser | Ile | Ser | Gln | Gly | Ile | |
| | | 275 | | | | | 280 | | | | | 285 | | | | |
| atg | acc | tat | gcc | aac | agt | gtg | gtg | tcc | gac | atg | atg | gtc | tcc | atc | atg | 912 |
| Met | Thr | Tyr | Ala | Asn | Ser | Val | Val | Ser | Asp | Met | Met | Val | Ser | Ile | Met | |
| | 290 | | | | | 295 | | | | | 300 | | | | | |
| aag | acc | ctg | aag | atc | cag | gtg | aag | gac | acg | acc | att | gcc | acc | atc | gtg | 960 |
| Lys | Thr | Leu | Lys | Ile | Gln | Val | Lys | Asp | Thr | Thr | Ile | Ala | Thr | Ile | Val | |
| 305 | | | | | 310 | | | | | 315 | | | | | 320 | |
| ctg | aag | aag | gtc | ctg | atc | aag | cac | gcc | aaa | gag | gtg | gtc | tcc | gac | ctc | 1008 |
| Leu | Lys | Lys | Val | Leu | Ile | Lys | His | Ala | Lys | Glu | Val | Val | Ser | Asp | Leu | |
| | | | 325 | | | | | 330 | | | | | 335 | | | |
| atc | gac | tcc | ttc | atg | aag | aac | ctc | cac | aac | gtc | acg | ggg | acc | ctc | atg | 1056 |
| Ile | Asp | Ser | Phe | Met | Lys | Asn | Leu | His | Asn | Val | Thr | Gly | Thr | Leu | Met | |
| | | | 340 | | | | | 345 | | | | | 350 | | | |
| acg | gac | acg | gac | ttt | gtc | tcg | gcc | gtg | aaa | aga | agc | ttc | ttc | tct | cat | 1104 |
| Thr | Asp | Thr | Asp | Phe | Val | Ser | Ala | Val | Lys | Arg | Ser | Phe | Phe | Ser | His | |
| | | 355 | | | | | 360 | | | | | 365 | | | | |
| gga | agc | cag | aag | gcc | acg | gac | atc | atg | gac | gcc | atg | ctg | ggg | aaa | ctc | 1152 |
| Gly | Ser | Gln | Lys | Ala | Thr | Asp | Ile | Met | Asp | Ala | Met | Leu | Gly | Lys | Leu | |
| | 370 | | | | | 375 | | | | | 380 | | | | | |
| tat | tcg | gtg | ata | ttt | gcc | aag | aaa | ccc | cct | gag | aca | gtc | agg | aaa | acc | 1200 |
| Tyr | Ser | Val | Ile | Phe | Ala | Lys | Lys | Pro | Pro | Glu | Thr | Val | Arg | Lys | Thr | |
| 385 | | | | | 390 | | | | | 395 | | | | | 400 | |
| aag | gat | aag | tct | gaa | agt | tac | tcc | ctc | gtc | tct | atg | aaa | ggg | atg | ggt | 1248 |
| Lys | Asp | Lys | Ser | Glu | Ser | Tyr | Ser | Leu | Val | Ser | Met | Lys | Gly | Met | Gly | |
| | | | 405 | | | | | 410 | | | | | 415 | | | |
| gac | cct | aaa | cac | cga | aac | gtc | aac | ttc | gcc | tcc | atg | aaa | tca | gaa | ggt | 1296 |
| Asp | Pro | Lys | His | Arg | Asn | Val | Asn | Phe | Ala | Ser | Met | Lys | Ser | Glu | Gly | |
| | | | 420 | | | | | 425 | | | | | 430 | | | |
| aaa | gtg | agg | gag | aga | gta | tgc | acc | ccc | acg | ccc | aaa | ccc | gag | aag | tcc | 1344 |
| Lys | Val | Arg | Glu | Arg | Val | Cys | Thr | Pro | Thr | Pro | Lys | Pro | Glu | Lys | Ser | |
| | | 435 | | | | | 440 | | | | | 445 | | | | |
| tgt | gtg | gaa | act | ctg | ggg | gaa | cac | att | atc | aaa | gag | ggg | ctg | acc | ctg | 1392 |
| Cys | Val | Glu | Thr | Leu | Gly | Glu | His | Ile | Ile | Lys | Glu | Gly | Leu | Thr | Leu | |
| | 450 | | | | | 455 | | | | | 460 | | | | | |
| tgg | cac | aac | agc | cag | cag | aag | gaa | ggc | ata | tct | gca | tgc | ctc | cag | ggc | 1440 |
| Trp | His | Asn | Ser | Gln | Gln | Lys | Glu | Gly | Ile | Ser | Ala | Cys | Leu | Gln | Gly | |
| 465 | | | | | 470 | | | | | 475 | | | | | 480 | |
| tca | ccc | ttc | gtc | act | ccc | aaa | aga | cag | tat | aaa | cct | gtg | ccg | gac | ttt | 1488 |
| Ser | Pro | Phe | Val | Thr | Pro | Lys | Arg | Gln | Tyr | Lys | Pro | Val | Pro | Asp | Phe | |
| | | | 485 | | | | | 490 | | | | | 495 | | | |
| ccc | ctg | ggg | ttc | cct | ttt | gac | ccc | tgc | aac | ttc | agc | ctc | cct | atg | cag | 1536 |
| Pro | Leu | Gly | Phe | Pro | Phe | Asp | Pro | Cys | Asn | Phe | Ser | Leu | Pro | Met | Gln | |
| | | 500 | | | | | 505 | | | | | 510 | | | | |
| tgc | cca | gaa | aaa | cct | gag | aat | ttt | atg | tgc | gac | tca | gac | tcc | tgg | gcc | 1584 |
| Cys | Pro | Glu | Lys | Pro | Glu | Asn | Phe | Met | Cys | Asp | Ser | Asp | Ser | Trp | Ala | |
| | 515 | | | | | 520 | | | | | 525 | | | | | |
| aaa | gac | ctg | ctt | gtg | tct | gct | tta | ctt | ttg | atc | cag | tac | cac | ctg | gcc | 1632 |
| Lys | Asp | Leu | Leu | Val | Ser | Ala | Leu | Leu | Leu | Ile | Gln | Tyr | His | Leu | Ala | |
| 530 | | | | | 535 | | | | | 540 | | | | | | |
| cag | gga | gga | aac | atg | gat | gca | cag | agc | ttt | ctc | gaa | gct | gct | ggc | acc | 1680 |
| Gln | Gly | Gly | Asn | Met | Asp | Ala | Gln | Ser | Phe | Leu | Glu | Ala | Ala | Gly | Thr | |
| 545 | | | | | 550 | | | | | 555 | | | | | 560 | |
| tcc | aac | ctg | tat | ccc | act | aag | tct | cca | gcc | gtt | tcc | cat | gag | tcc | agc | 1728 |
| Ser | Asn | Leu | Tyr | Pro | Thr | Lys | Ser | Pro | Ala | Val | Ser | His | Glu | Ser | Ser | |
| | | | 565 | | | | | 570 | | | | | 575 | | | |
| ctc | cgg | tct | ccc | caa | gtg | gga | gct | gac | cca | gaa | gaa | gtg | gag | aag | aag | 1776 |

```
                Leu Arg Ser Pro Gln Val Gly Ala Asp Pro Glu Glu Val Glu Lys Lys
                        580                 585                 590 gac cta atg agc gtt ttc ttc aac ttt atc cgg aac ttg ctc agt gag       1824
Asp Leu Met Ser Val Phe Phe Asn Phe Ile Arg Asn Leu Leu Ser Glu
            595                 600                 605 acc att ttc aag agc gac cat agc tgt gat ccc aag gca acc aag gaa       1872
Thr Ile Phe Lys Ser Asp His Ser Cys Asp Pro Lys Ala Thr Lys Glu
        610                 615                 620 gac aac agc ccc cag tgt gaa aga ccc gtc acc cct tct ccc gcc aaa       1920
Asp Asn Ser Pro Gln Cys Glu Arg Pro Val Thr Pro Ser Pro Ala Lys
625                 630                 635                 640 tta aat gaa tgt gat gag act ggg ggt gct ttt gcg ggg ctc acc aag       1968
Leu Asn Glu Cys Asp Glu Thr Gly Gly Ala Phe Ala Gly Leu Thr Lys
                645                 650                 655 atg gtg gct aac aaa ctt gat ggc cac atg aac ggg cag atg gta gac       2016
Met Val Ala Asn Lys Leu Asp Gly His Met Asn Gly Gln Met Val Asp
            660                 665                 670 cat ctg atg gac tca gtg atg aag ttg tgt ctc atc att gcc aag tcc       2064
His Leu Met Asp Ser Val Met Lys Leu Cys Leu Ile Ile Ala Lys Ser
        675                 680                 685 tgc gac tct cca ttg gca gaa ctg gga gac gac aag tct ggg gat gcc       2112
Cys Asp Ser Pro Leu Ala Glu Leu Gly Asp Asp Lys Ser Gly Asp Ala
690                 695                 700 agc agg cca aca tca gcc ttc cca gag agt tta tat gag tgt ttg tcc       2160
Ser Arg Pro Thr Ser Ala Phe Pro Glu Ser Leu Tyr Glu Cys Leu Ser
705                 710                 715                 720 acc aag ggc aca ggg act gca gag aca ttc cta cag aat gcc tat cag       2208
Thr Lys Gly Thr Gly Thr Ala Glu Thr Phe Leu Gln Asn Ala Tyr Gln
                725                 730                 735 gct atc cac aac gaa ctg agg agt cta tca gca cag ccc cca gaa ggg       2256
Ala Ile His Asn Glu Leu Arg Ser Leu Ser Ala Gln Pro Pro Glu Gly
            740                 745                 750 tgc aca gca ccc aaa gtg atc gtc agc aac cac aac ctg act gac acc       2304
Cys Thr Ala Pro Lys Val Ile Val Ser Asn His Asn Leu Thr Asp Thr
        755                 760                 765 gtg cag aac aag cag ctc caa gcc gtt ctt cag tgg gtg gcc gcc tct       2352
Val Gln Asn Lys Gln Leu Gln Ala Val Leu Gln Trp Val Ala Ala Ser
770                 775                 780 gag ctc aac gtc ccc att ctg tac ttt gcg ggt gac gac gaa gga atc       2400
Glu Leu Asn Val Pro Ile Leu Tyr Phe Ala Gly Asp Asp Glu Gly Ile
785                 790                 795                 800 cag gag aag cta ctt cag ctc tcg gca gct gcc gtg gaa aag ggg cgc       2448
Gln Glu Lys Leu Leu Gln Leu Ser Ala Ala Ala Val Glu Lys Gly Arg
                805                 810                 815 agc gta ggt gag gtt cta cag tcg gtg ctg cgg tac gag aag gag cga       2496
Ser Val Gly Glu Val Leu Gln Ser Val Leu Arg Tyr Glu Lys Glu Arg
            820                 825                 830 cag ctg gac gag gcg gtg ggc aac gtc aca cgg ctg cag ctg ctg gac       2544
Gln Leu Asp Glu Ala Val Gly Asn Val Thr Arg Leu Gln Leu Leu Asp
        835                 840                 845 tgg ctg atg gtg aac ctg                                               2562
Trp Leu Met Val Asn Leu
        850

<210> SEQ ID NO 13
<211> LENGTH: 854
<212> TYPE: PRT
<213> ORGANISM: Bos sp.

<400> SEQUENCE: 13
```

```
Val Asp Trp Leu Gln Ser Gln Asn Gly Val Cys Lys Val Asp Val Tyr
 1               5                  10                  15

Ser Pro Gly Asp Ser Gln Pro Gln Asp Trp Lys Met Ser Asp Glu Ser
            20                  25                  30

Leu Ser Ile Phe Lys Glu Ala Ser His Asp Pro Ile Arg Val Leu Ser
         35                  40                  45

Trp Leu Arg Arg Asp Leu Glu Lys Ser Thr Ala Gly Phe Gln Asp Ile
     50                  55                  60

Arg Phe Lys Pro Gly Glu Ser Ser Leu Gly Arg Glu Met Val Ser Ser
 65              70                  75                      80

Gly Asp Pro Arg Lys Gly Phe Cys Val Asp Tyr Tyr Asn Thr Thr Ser
                 85                  90                  95

Arg Gly Ser Pro Gly Arg Leu His Phe Glu Met Ser His Arg Glu Asn
            100                 105                 110

Pro His Gln Gly Pro Thr Cys Asn Gly Ser Ser Val Asp Glu Val Ser
            115                 120                 125

Phe Tyr Ala Asn Arg Leu Thr Asn Leu Val Ile Ala Met Ala Arg Lys
     130                 135                 140

Glu Ile Asn Glu Lys Ile Asp Gly Ser Glu Asn Arg Cys Val His Gln
145                 150                 155                 160

Ser Val Tyr Met Gly Asp Glu Pro Pro Asn Lys Ser Leu Ser Lys
                165                 170                 175

Val Ala Ser Glu Leu Val Asn Glu Thr Val Thr Ala Cys Ser Lys Asn
            180                 185                 190

Thr Pro Ser Asp Lys Ala Pro Gly Ser Gly Asp Arg Ala Ser Gly Thr
         195                 200                 205

Leu Gln Ser Pro Pro Asn Leu Lys Tyr Lys Ser Thr Leu Lys Ile Lys
     210                 215                 220

Glu Ser Asn Lys Gly Gly Arg Gly Pro Asp Asp Arg Pro Ser Ser Lys
225                 230                 235                 240

Lys Ser Leu Phe Tyr Lys Glu Val Phe Glu Ser Arg Asn Ala Gly Asp
             245                 250                 255

Ala Lys Glu Gly Gly Arg Thr Leu Pro Ala Glu Arg Lys Met Phe Arg
         260                 265                 270

Gly Tyr Glu Arg Pro Asp Asp Phe Thr Ala Ser Ile Ser Gln Gly Ile
     275                 280                 285

Met Thr Tyr Ala Asn Ser Val Val Ser Asp Met Met Val Ser Ile Met
290                 295                 300

Lys Thr Leu Lys Ile Gln Val Lys Asp Thr Thr Ile Ala Thr Ile Val
305                 310                 315                 320

Leu Lys Lys Val Leu Ile Lys His Ala Lys Glu Val Val Ser Asp Leu
             325                 330                 335

Ile Asp Ser Phe Met Lys Asn Leu His Asn Val Thr Gly Thr Leu Met
         340                 345                 350

Thr Asp Thr Asp Phe Val Ser Ala Val Lys Arg Ser Phe Phe Ser His
     355                 360                 365

Gly Ser Gln Lys Ala Thr Asp Ile Met Asp Ala Met Leu Gly Lys Leu
 370                 375                 380

Tyr Ser Val Ile Phe Ala Lys Lys Pro Pro Glu Thr Val Arg Lys Thr
385                 390                 395                 400

Lys Asp Lys Ser Glu Ser Tyr Ser Leu Val Ser Met Lys Gly Met Gly
             405                 410                 415

Asp Pro Lys His Arg Asn Val Asn Phe Ala Ser Met Lys Ser Glu Gly
```

-continued

```
                420                 425                 430
Lys Val Arg Glu Arg Val Cys Thr Pro Thr Lys Pro Glu Lys Ser
                435                 440                 445
Cys Val Glu Thr Leu Gly Glu His Ile Ile Lys Glu Gly Leu Thr Leu
            450                 455                 460
Trp His Asn Ser Gln Gln Lys Glu Gly Ile Ser Ala Cys Leu Gln Gly
465                 470                 475                 480
Ser Pro Phe Val Thr Pro Lys Arg Gln Tyr Lys Pro Val Pro Asp Phe
                485                 490                 495
Pro Leu Gly Phe Pro Phe Asp Pro Cys Asn Phe Ser Leu Pro Met Gln
                500                 505                 510
Cys Pro Glu Lys Pro Glu Asn Phe Met Cys Asp Ser Asp Ser Trp Ala
            515                 520                 525
Lys Asp Leu Leu Val Ser Ala Leu Leu Leu Ile Gln Tyr His Leu Ala
            530                 535                 540
Gln Gly Gly Asn Met Asp Ala Gln Ser Phe Leu Glu Ala Ala Gly Thr
545                 550                 555                 560
Ser Asn Leu Tyr Pro Thr Lys Ser Pro Ala Val Ser His Glu Ser Ser
                565                 570                 575
Leu Arg Ser Pro Gln Val Gly Ala Asp Pro Glu Glu Val Glu Lys Lys
            580                 585                 590
Asp Leu Met Ser Val Phe Phe Asn Phe Ile Arg Asn Leu Leu Ser Glu
            595                 600                 605
Thr Ile Phe Lys Ser Asp His Ser Cys Asp Pro Lys Ala Thr Lys Glu
            610                 615                 620
Asp Asn Ser Pro Gln Cys Glu Arg Pro Val Thr Pro Ser Pro Ala Lys
625                 630                 635                 640
Leu Asn Glu Cys Asp Glu Thr Gly Gly Ala Phe Ala Gly Leu Thr Lys
                645                 650                 655
Met Val Ala Asn Lys Leu Asp Gly His Met Asn Gly Gln Met Val Asp
                660                 665                 670
His Leu Met Asp Ser Val Met Lys Leu Cys Leu Ile Ile Ala Lys Ser
            675                 680                 685
Cys Asp Ser Pro Leu Ala Glu Leu Gly Asp Asp Lys Ser Gly Asp Ala
            690                 695                 700
Ser Arg Pro Thr Ser Ala Phe Pro Glu Ser Leu Tyr Glu Cys Leu Ser
705                 710                 715                 720
Thr Lys Gly Thr Gly Thr Ala Glu Thr Phe Leu Gln Asn Ala Tyr Gln
                725                 730                 735
Ala Ile His Asn Glu Leu Arg Ser Leu Ser Ala Gln Pro Pro Glu Gly
            740                 745                 750
Cys Thr Ala Pro Lys Val Ile Val Ser Asn His Asn Leu Thr Asp Thr
            755                 760                 765
Val Gln Asn Lys Gln Leu Gln Ala Val Leu Gln Trp Val Ala Ala Ser
            770                 775                 780
Glu Leu Asn Val Pro Ile Leu Tyr Phe Ala Gly Asp Asp Glu Gly Ile
785                 790                 795                 800
Gln Glu Lys Leu Leu Gln Leu Ser Ala Ala Val Glu Lys Gly Arg
                805                 810                 815
Ser Val Gly Glu Val Leu Gln Ser Val Leu Arg Tyr Glu Lys Glu Arg
            820                 825                 830
Gln Leu Asp Glu Ala Val Gly Asn Val Thr Arg Leu Gln Leu Leu Asp
            835                 840                 845
```

```
Trp Leu Met Val Asn Leu
    850
```

```
<210> SEQ ID NO 14
<211> LENGTH: 3014
<212> TYPE: DNA
<213> ORGANISM: Homo sapiens
<220> FEATURE:
<221> NAME/KEY: CDS
<222> LOCATION: (230)..(2788)
<220> FEATURE:
<221> NAME/KEY: 5'UTR
<222> LOCATION: (1)..(229)
<220> FEATURE:
<221> NAME/KEY: 3'UTR
<222> LOCATION: (2789)..(3014)

<400> SEQUENCE: 14
```

| | |
|---|---:|
| ggtacatgga aggccacagg aagaaacaag atcttgagct gagcaagaac atcccagcat | 60 |
| cttcattgac tttaaaagta tattctggag tcttccgtgg ttcactattc cagtactaca | 120 |
| gagattcctt atattacatg gcaggagggg ggtaaactga gggatagtga agacaacaat | 180 |
| aaattaatca agagctttcc tcatatctca gaacctatcc tctgtaaga atg tca gaa | 238 |

```
                                                    Met Ser Glu
                                                      1
aag gtt gac tgg tta caa agc caa aat gga gta tgc aaa gtt gat gtc    286
Lys Val Asp Trp Leu Gln Ser Gln Asn Gly Val Cys Lys Val Asp Val
     5                  10                  15 tat tct cct gga gac aac caa gcc cag gac tgg aaa atg gac acc tcc    334
Tyr Ser Pro Gly Asp Asn Gln Ala Gln Asp Trp Lys Met Asp Thr Ser
 20                  25                  30                  35 acg gat cct gtc aga gtg ctc agc tgg ctc cgc aga gac ctg gag aag    382
Thr Asp Pro Val Arg Val Leu Ser Trp Leu Arg Arg Asp Leu Glu Lys
                 40                  45                  50 agt aca gca gag ttc caa gat gtt cgg ttc aaa ccc gga gaa tca ttt    430
Ser Thr Ala Glu Phe Gln Asp Val Arg Phe Lys Pro Gly Glu Ser Phe
             55                  60                  65 ggt ggg gaa acg tcc aac tca gga gac cca cac aaa ggt ttc tct gta    478
Gly Gly Glu Thr Ser Asn Ser Gly Asp Pro His Lys Gly Phe Ser Val
         70                  75                  80 gac tat tac aac acc acc acc aag ggc act cca gaa aga ttg cat ttt    526
Asp Tyr Tyr Asn Thr Thr Thr Lys Gly Thr Pro Glu Arg Leu His Phe
 85                  90                  95 gag atg act cac aaa gag att cct tgc cag ggc ccc agg gcc caa ctt    574
Glu Met Thr His Lys Glu Ile Pro Cys Gln Gly Pro Arg Ala Gln Leu
100                 105                 110                 115 ggc aac ggg agt tca gta gat gaa gtt tcc ttc tat gct aac cgc ctc    622
Gly Asn Gly Ser Ser Val Asp Glu Val Ser Phe Tyr Ala Asn Arg Leu
                120                 125                 130 acg aat cta gtc ata gcc atg gcc cgc aaa gag atc aat gag aag atc    670
Thr Asn Leu Val Ile Ala Met Ala Arg Lys Glu Ile Asn Glu Lys Ile
            135                 140                 145 gat ggc tct gaa aac aaa tgt gtc tat cag tca ttg tac atg ggg aat    718
Asp Gly Ser Glu Asn Lys Cys Val Tyr Gln Ser Leu Tyr Met Gly Asn
        150                 155                 160 gaa ccc aca ccc acc aaa agc ctc agt aag ata gca tca gag ctt gtg    766
Glu Pro Thr Pro Thr Lys Ser Leu Ser Lys Ile Ala Ser Glu Leu Val
    165                 170                 175 aat gag acc gtc tct gca tgt tcc agg aat gct gcc cca gac aag gct    814
Asn Glu Thr Val Ser Ala Cys Ser Arg Asn Ala Ala Pro Asp Lys Ala
180                 185                 190                 195
```

-continued

| | | |
|---|---|---|
| cct ggc tct gga gac aga gtc tca gga tca tca caa agt ccc cca aat<br>Pro Gly Ser Gly Asp Arg Val Ser Gly Ser Ser Gln Ser Pro Pro Asn<br>    200                 205                 210 | | 862 |
| ttg aaa tac aag tcc act ttg aag atc aag gag agc acc aaa gaa aga<br>Leu Lys Tyr Lys Ser Thr Leu Lys Ile Lys Glu Ser Thr Lys Glu Arg<br>        215                 220                 225 | | 910 |
| cag ggt cca gat gac aag cct cct tct aag aag tct ttc ttc tat aag<br>Gln Gly Pro Asp Asp Lys Pro Pro Ser Lys Lys Ser Phe Phe Tyr Lys<br>            230                 235                 240 | | 958 |
| gaa gtg ttt gaa tct cgt aac gga gat tat gcc aga gag ggt gga agg<br>Glu Val Phe Glu Ser Arg Asn Gly Asp Tyr Ala Arg Glu Gly Gly Arg<br>245                 250                 255 | | 1006 |
| ttc ttt cct cgg gag aga aag agg ttt cga ggg cag gaa agg cct gat<br>Phe Phe Pro Arg Glu Arg Lys Arg Phe Arg Gly Gln Glu Arg Pro Asp<br>260                 265                 270                 275 | | 1054 |
| gac ttt acg gct tct gtt agt gaa ggg atc atg acc tat gct aac agt<br>Asp Phe Thr Ala Ser Val Ser Glu Gly Ile Met Thr Tyr Ala Asn Ser<br>                280                 285                 290 | | 1102 |
| gtg gta tct gat atg atg gtc tcc atc atg aag aca ctg aag atc caa<br>Val Val Ser Asp Met Met Val Ser Ile Met Lys Thr Leu Lys Ile Gln<br>                    295                 300                 305 | | 1150 |
| gtg aaa gac aca acc att gcc acc atc cta ctg aag aag gtt ctg ctc<br>Val Lys Asp Thr Thr Ile Ala Thr Ile Leu Leu Lys Lys Val Leu Leu<br>        310                 315                 320 | | 1198 |
| aag cat gca aaa gag gtg gtc tcg gat ctc atc gac tcc ttc ttg agg<br>Lys His Ala Lys Glu Val Val Ser Asp Leu Ile Asp Ser Phe Leu Arg<br>325                 330                 335 | | 1246 |
| aat ctc cac agc gtc aca ggg acc ctc atg act gac aca cag ttt gtc<br>Asn Leu His Ser Val Thr Gly Thr Leu Met Thr Asp Thr Gln Phe Val<br>340                 345                 350                 355 | | 1294 |
| tcg gct gtg aaa aga act gtc ttc tct cat gga agc caa aag gcc aca<br>Ser Ala Val Lys Arg Thr Val Phe Ser His Gly Ser Gln Lys Ala Thr<br>                360                 365                 370 | | 1342 |
| gat atc atg gat gcc atg cta agg aag ctg tac aat gta atg ttt gcc<br>Asp Ile Met Asp Ala Met Leu Arg Lys Leu Tyr Asn Val Met Phe Ala<br>                    375                 380                 385 | | 1390 |
| aag aaa gtc cct gag cat gtc agg aaa gcc caa gac aag gct gag agt<br>Lys Lys Val Pro Glu His Val Arg Lys Ala Gln Asp Lys Ala Glu Ser<br>        390                 395                 400 | | 1438 |
| tat tcc ctc atc tcc atg aaa gga atg ggt gat cct aaa aac cga aat<br>Tyr Ser Leu Ile Ser Met Lys Gly Met Gly Asp Pro Lys Asn Arg Asn<br>405                 410                 415 | | 1486 |
| gtg aac ttt gcc atg aaa tct gaa act aaa ttg aga gaa aaa atg tat<br>Val Asn Phe Ala Met Lys Ser Glu Thr Lys Leu Arg Glu Lys Met Tyr<br>420                 425                 430                 435 | | 1534 |
| tct gaa ccc aaa tca gag gag gag act tgt gcg aaa act ctg ggt gag<br>Ser Glu Pro Lys Ser Glu Glu Glu Thr Cys Ala Lys Thr Leu Gly Glu<br>                440                 445                 450 | | 1582 |
| cac att atc aaa gag ggg ctt acc ctg tgg cat aaa agt cag cag aaa<br>His Ile Ile Lys Glu Gly Leu Thr Leu Trp His Lys Ser Gln Gln Lys<br>                    455                 460                 465 | | 1630 |
| gaa tgt aaa tct cta ggt ttc cag cat gca gca ttc gaa gct ccc aac<br>Glu Cys Lys Ser Leu Gly Phe Gln His Ala Ala Phe Glu Ala Pro Asn<br>        470                 475                 480 | | 1678 |
| aca cag cgt aag cct gca tca gac att tcc ttt gag tac cct gaa gat<br>Thr Gln Arg Lys Pro Ala Ser Asp Ile Ser Phe Glu Tyr Pro Glu Asp<br>485                 490                 495 | | 1726 |
| att ggc aac ctc agc ctt cct cca tat cct cca gag aaa cct gag aat<br>Ile Gly Asn Leu Ser Leu Pro Pro Tyr Pro Pro Glu Lys Pro Glu Asn<br>500                 505                 510                 515 | | 1774 |

```
ttt atg tat gat tca gac tcc tgg gcc aag gac ctg atc gtg tct gcc    1822
Phe Met Tyr Asp Ser Asp Ser Trp Ala Lys Asp Leu Ile Val Ser Ala
            520                 525                 530 ctg ctt ctg att caa tat cac ctg gcc cag gga gga aga agg gat gca    1870
Leu Leu Leu Ile Gln Tyr His Leu Ala Gln Gly Gly Arg Arg Asp Ala
            535                 540                 545 cgg agc ttc gtt gaa gct gct ggc acc acc aac ttt cct gcc aat gaa    1918
Arg Ser Phe Val Glu Ala Ala Gly Thr Thr Asn Phe Pro Ala Asn Glu
            550                 555                 560 cct cct gta gct ccc gat gaa tct tgc ctt aag tct gct ccc att gta    1966
Pro Pro Val Ala Pro Asp Glu Ser Cys Leu Lys Ser Ala Pro Ile Val
565                 570                 575 ggt gac caa gaa caa gca gaa aag aag gac cta agg agt gtt ttc ttt    2014
Gly Asp Gln Glu Gln Ala Glu Lys Lys Asp Leu Arg Ser Val Phe Phe
580                 585                 590                 595 aat ttc atc cgg aac tta ctt agt gag acc att ttc aag cgt gac cag    2062
Asn Phe Ile Arg Asn Leu Leu Ser Glu Thr Ile Phe Lys Arg Asp Gln
            600                 605                 610 agc cct gaa ccc aag gtg ccg gaa cag cca gtt aag gaa gat agg aag    2110
Ser Pro Glu Pro Lys Val Pro Glu Gln Pro Val Lys Glu Asp Arg Lys
            615                 620                 625 ttg tgt gaa aga ccg ttg gcg tct tct ccc ccc agg cta tat gag gat    2158
Leu Cys Glu Arg Pro Leu Ala Ser Ser Pro Pro Arg Leu Tyr Glu Asp
            630                 635                 640 gat gag acc cct ggt gcc ctt tct ggg ctg acc aag atg gct gtc agc    2206
Asp Glu Thr Pro Gly Ala Leu Ser Gly Leu Thr Lys Met Ala Val Ser
            645                 650                 655 cag ata gat ggc cac atg agt ggg cag atg gta gaa cat ctg atg aac    2254
Gln Ile Asp Gly His Met Ser Gly Gln Met Val Glu His Leu Met Asn
660                 665                 670                 675 tca gtg atg aag ctg tgt gtc atc att gct aag tcc tgt gat gct tcg    2302
Ser Val Met Lys Leu Cys Val Ile Ile Ala Lys Ser Cys Asp Ala Ser
            680                 685                 690 ttg gca gag ctg gga gat gac aag tct gga gat gcc agt agg cta act    2350
Leu Ala Glu Leu Gly Asp Asp Lys Ser Gly Asp Ala Ser Arg Leu Thr
            695                 700                 705 tcg gcc ttc cca gat agt tta tat gag tgc tta cca gcc aag ggc aca    2398
Ser Ala Phe Pro Asp Ser Leu Tyr Glu Cys Leu Pro Ala Lys Gly Thr
            710                 715                 720 ggg tca gca gaa gct gtc ctg cag aat gcc tat caa gct atc cat aat    2446
Gly Ser Ala Glu Ala Val Leu Gln Asn Ala Tyr Gln Ala Ile His Asn
            725                 730                 735 gaa atg aga ggc aca tca gga cag ccc cct gaa ggg tgt gca gca ccc    2494
Glu Met Arg Gly Thr Ser Gly Gln Pro Pro Glu Gly Cys Ala Ala Pro
740                 745                 750                 755 acg gtg att gtc agc aat cac aac cta acg gac aca gtt cag aac aag    2542
Thr Val Ile Val Ser Asn His Asn Leu Thr Asp Thr Val Gln Asn Lys
            760                 765                 770 caa ctc caa gcc gtc ctt caa tgg gta gct gcc tct gag ctc aat gtc    2590
Gln Leu Gln Ala Val Leu Gln Trp Val Ala Ala Ser Glu Leu Asn Val
            775                 780                 785 cct att ttg tat ttt gct ggt gat gat gaa ggg atc cag gag aag cta    2638
Pro Ile Leu Tyr Phe Ala Gly Asp Asp Glu Gly Ile Gln Glu Lys Leu
            790                 795                 800 ctt cag ctc tca gct gct gct gtg gac aaa gga tgc agt gtg ggc gag    2686
Leu Gln Leu Ser Ala Ala Ala Val Asp Lys Gly Cys Ser Val Gly Glu
            805                 810                 815 gtt ctg cag tcg gtg ctg cgc tat gag aag gag cgc cag ctg aat gag    2734
Val Leu Gln Ser Val Leu Arg Tyr Glu Lys Glu Arg Gln Leu Asn Glu
```

```
                820                 825                 830                 835
gcg gtg ggg aat gtc aca ccg ctg cag ctg ctg gac tgg ctg atg gtg       2782
Ala Val Gly Asn Val Thr Pro Leu Gln Leu Leu Asp Trp Leu Met Val
                    840                 845                 850 aac ctg taatcggcaa ccccactgct ttccctctt ctggcagtgg ggccggccct         2838
Asn Leu tatccccgcc cttctttctc acttccacat ctcccctct atatcctcac agagccctaa      2898
cattatcttc acaccactct catcaaagac atgtcatctt gtgctagcca ctggattttg     2958
cagattttcc tgtccatgca agcaaggacg taaaattaaa aaattacaat taaaaa         3014

<210> SEQ ID NO 15
<211> LENGTH: 853
<212> TYPE: PRT
<213> ORGANISM: Homo sapiens

<400> SEQUENCE: 15

Met Ser Glu Lys Val Asp Trp Leu Gln Ser Gln Asn Gly Val Cys Lys
 1               5                  10                  15

Val Asp Val Tyr Ser Pro Gly Asp Asn Gln Ala Gln Asp Trp Lys Met
                20                  25                  30

Asp Thr Ser Thr Asp Pro Val Arg Val Leu Ser Trp Leu Arg Arg Asp
            35                  40                  45

Leu Glu Lys Ser Thr Ala Glu Phe Gln Asp Val Arg Phe Lys Pro Gly
        50                  55                  60

Glu Ser Phe Gly Gly Glu Thr Ser Asn Ser Gly Asp Pro His Lys Gly
 65                  70                  75                  80

Phe Ser Val Asp Tyr Tyr Asn Thr Thr Thr Lys Gly Thr Pro Glu Arg
                85                  90                  95

Leu His Phe Glu Met Thr His Lys Glu Ile Pro Cys Gln Gly Pro Arg
           100                 105                 110

Ala Gln Leu Gly Asn Gly Ser Ser Val Asp Glu Val Ser Phe Tyr Ala
        115                 120                 125

Asn Arg Leu Thr Asn Leu Val Ile Ala Met Ala Arg Lys Glu Ile Asn
130                 135                 140

Glu Lys Ile Asp Gly Ser Glu Asn Lys Cys Val Tyr Gln Ser Leu Tyr
145                 150                 155                 160

Met Gly Asn Glu Pro Thr Pro Thr Lys Ser Leu Ser Lys Ile Ala Ser
                165                 170                 175

Glu Leu Val Asn Glu Thr Val Ser Ala Cys Ser Arg Asn Ala Ala Pro
            180                 185                 190

Asp Lys Ala Pro Gly Ser Gly Asp Arg Val Ser Gly Ser Ser Gln Ser
        195                 200                 205

Pro Pro Asn Leu Lys Tyr Lys Ser Thr Leu Lys Ile Lys Glu Ser Thr
    210                 215                 220

Lys Glu Arg Gln Gly Pro Asp Asp Lys Pro Ser Lys Lys Ser Phe
225                 230                 235                 240

Phe Tyr Lys Glu Val Phe Glu Ser Arg Asn Gly Asp Tyr Ala Arg Glu
                245                 250                 255

Gly Gly Arg Phe Phe Pro Arg Glu Arg Lys Arg Phe Arg Gly Gln Glu
            260                 265                 270

Arg Pro Asp Asp Phe Thr Ala Ser Val Ser Glu Gly Ile Met Thr Tyr
        275                 280                 285

Ala Asn Ser Val Val Ser Asp Met Met Val Ser Ile Met Lys Thr Leu
```

-continued

```
            290                 295                 300
Lys Ile Gln Val Lys Asp Thr Thr Ile Ala Thr Ile Leu Leu Lys Lys
305                 310                 315                 320
Val Leu Leu Lys His Ala Lys Glu Val Val Ser Asp Leu Ile Asp Ser
                325                 330                 335
Phe Leu Arg Asn Leu His Ser Val Thr Gly Thr Leu Met Thr Asp Thr
                340                 345                 350
Gln Phe Val Ser Ala Val Lys Arg Thr Val Phe Ser His Gly Ser Gln
                355                 360                 365
Lys Ala Thr Asp Ile Met Asp Ala Met Leu Arg Lys Leu Tyr Asn Val
370                 375                 380
Met Phe Ala Lys Lys Val Pro Glu His Val Arg Lys Ala Gln Asp Lys
385                 390                 395                 400
Ala Glu Ser Tyr Ser Leu Ile Ser Met Lys Gly Met Gly Asp Pro Lys
                405                 410                 415
Asn Arg Asn Val Asn Phe Ala Met Lys Ser Glu Thr Lys Leu Arg Glu
                420                 425                 430
Lys Met Tyr Ser Glu Pro Lys Ser Glu Glu Thr Cys Ala Lys Thr
                435                 440                 445
Leu Gly Glu His Ile Ile Lys Glu Gly Leu Thr Leu Trp His Lys Ser
450                 455                 460
Gln Gln Lys Glu Cys Lys Ser Leu Gly Phe Gln His Ala Ala Phe Glu
465                 470                 475                 480
Ala Pro Asn Thr Gln Arg Lys Pro Ala Ser Asp Ile Ser Phe Glu Tyr
                485                 490                 495
Pro Glu Asp Ile Gly Asn Leu Ser Leu Pro Pro Tyr Pro Pro Glu Lys
                500                 505                 510
Pro Glu Asn Phe Met Tyr Asp Ser Asp Ser Trp Ala Lys Asp Leu Ile
                515                 520                 525
Val Ser Ala Leu Leu Ile Gln Tyr His Leu Ala Gln Gly Gly Arg
530                 535                 540
Arg Asp Ala Arg Ser Phe Val Glu Ala Ala Gly Thr Thr Asn Phe Pro
545                 550                 555                 560
Ala Asn Glu Pro Pro Val Ala Pro Asp Glu Ser Cys Leu Lys Ser Ala
                565                 570                 575
Pro Ile Val Gly Asp Gln Glu Gln Ala Glu Lys Lys Asp Leu Arg Ser
                580                 585                 590
Val Phe Phe Asn Phe Ile Arg Asn Leu Leu Ser Glu Thr Ile Phe Lys
                595                 600                 605
Arg Asp Gln Ser Pro Glu Pro Lys Val Pro Glu Gln Pro Val Lys Glu
610                 615                 620
Asp Arg Lys Leu Cys Glu Arg Pro Leu Ala Ser Ser Pro Arg Leu
625                 630                 635                 640
Tyr Glu Asp Asp Glu Thr Pro Gly Ala Leu Ser Gly Leu Thr Lys Met
                645                 650                 655
Ala Val Ser Gln Ile Asp Gly His Met Ser Gly Gln Met Val Glu His
                660                 665                 670
Leu Met Asn Ser Val Met Lys Leu Cys Val Ile Ile Ala Lys Ser Cys
                675                 680                 685
Asp Ala Ser Leu Ala Glu Leu Gly Asp Asp Lys Ser Gly Asp Ala Ser
                690                 695                 700
Arg Leu Thr Ser Ala Phe Pro Asp Ser Leu Tyr Glu Cys Leu Pro Ala
705                 710                 715                 720
```

```
Lys Gly Thr Gly Ser Ala Glu Ala Val Leu Gln Asn Ala Tyr Gln Ala
                725                 730                 735

Ile His Asn Glu Met Arg Gly Thr Ser Gly Gln Pro Pro Glu Gly Cys
            740                 745                 750

Ala Ala Pro Thr Val Ile Val Ser Asn His Asn Leu Thr Asp Thr Val
            755                 760             765

Gln Asn Lys Gln Leu Gln Ala Val Leu Gln Trp Val Ala Ser Glu
    770             775                 780

Leu Asn Val Pro Ile Leu Tyr Phe Ala Gly Asp Asp Glu Gly Ile Gln
785                 790                 795                 800

Glu Lys Leu Leu Gln Leu Ser Ala Ala Val Asp Lys Gly Cys Ser
            805                 810                 815

Val Gly Glu Val Leu Gln Ser Val Leu Arg Tyr Glu Lys Glu Arg Gln
            820                 825                 830

Leu Asn Glu Ala Val Gly Asn Val Thr Pro Leu Gln Leu Leu Asp Trp
            835                 840                 845

Leu Met Val Asn Leu
    850
```

<210> SEQ ID NO 16
<211> LENGTH: 12
<212> TYPE: PRT
<213> ORGANISM: Mus musculus

<400> SEQUENCE: 16

```
Ser Phe Tyr Ala Asn Arg Leu Thr Asn Leu Val Ile
  1               5                  10
```

<210> SEQ ID NO 17
<211> LENGTH: 18
<212> TYPE: PRT
<213> ORGANISM: Artificial Sequence
<220> FEATURE:
<223> OTHER INFORMATION: Description of Artificial Sequence: This is a
      consensus sequence of the RII subunit binding site
      of AKAP110 from several tissue types
<220> FEATURE:
<221> NAME/KEY: VARIANT
<222> LOCATION: (1)..(2)
<223> OTHER INFORMATION: The second amino acid in the sequence is
      selected from leucine, isoleucine and valine
<220> FEATURE:
<221> NAME/KEY: VARIANT
<222> LOCATION: (5)..(6)
<223> OTHER INFORMATION: The amino acid at position 6 in the sequence
      is selected from alanine and serine
<220> FEATURE:
<221> NAME/KEY: VARIANT
<222> LOCATION: (9)..(10)
<223> OTHER INFORMATION: The amino acids at positions 9 and 10 in the
      sequence are independently selected from leucine,
      isoleucine and valine
<220> FEATURE:
<221> NAME/KEY: VARIANT
<222> LOCATION: (13)..(14)
<223> OTHER INFORMATION: The amino acid at positions 13 and 14 are
      independently selected from leucine, isoleucine
      and valine
<220> FEATURE:
<221> NAME/KEY: VARIANT
<222> LOCATION: (16)..(17)
<223> OTHER INFORMATION: The amino acid at position 17 in the sequence
      is selected from alanine and serine
<220> FEATURE:
<221> NAME/KEY: VARIANT
<222> LOCATION: (17)..(18)
<223> OTHER INFORMATION: The amino acid at position 18 in the sequence is selected from leucine, isoleucine and valine

<400> SEQUENCE: 17

Xaa Xaa Xaa Xaa Xaa Xaa Xaa Xaa Xaa Xaa Xaa Xaa Xaa Xaa Xaa
1               5                   10                  15

Xaa Xaa

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: antisense
      oligonucleotide comprising sequence complementary
      to the translation initiation codon of human
      akap110

<400> SEQUENCE: 18
gctttgtaac cagtcaacct tttctgacat                                    30

<210> SEQ ID NO 19
<211> LENGTH: 18
<212> TYPE: PRT
<213> ORGANISM: Bos sp.

<400> SEQUENCE: 19

Glu Val Ser Phe Tyr Ala Asn Arg Leu Thr Asn Leu Val Ile Ala Met
1               5                   10                  15

Ala Arg

<210> SEQ ID NO 20
<211> LENGTH: 18
<212> TYPE: PRT
<213> ORGANISM: Bos sp.

<400> SEQUENCE: 20

Asp Val Ser Phe Tyr Val Asn Arg Leu Thr Ser Leu Val Ile Gln Met
1               5                   10                  15

Ala Arg

<210> SEQ ID NO 21
<211> LENGTH: 18
<212> TYPE: PRT
<213> ORGANISM: Bos sp.

<400> SEQUENCE: 21

Glu Ile Lys Arg Ala Ala Phe Gln Ile Ile Ser Gln Val Ile Ser Glu
1               5                   10                  15

Ala Thr

<210> SEQ ID NO 22
<211> LENGTH: 18
<212> TYPE: PRT
<213> ORGANISM: Bos sp.

<400> SEQUENCE: 22

Arg Met Asn Glu Ile Ala Arg Thr Val Val Glu Gly Val Leu Ala Ala
1               5                   10                  15

Ser Val

<210> SEQ ID NO 23
<211> LENGTH: 18

```
<212> TYPE: PRT
<213> ORGANISM: Bos sp.

<400> SEQUENCE: 23

Thr Ala Glu Glu Val Ser Ala Arg Ile Val Gln Val Val Thr Ala Glu
 1               5                  10                  15
Ala Val

<210> SEQ ID NO 24
<211> LENGTH: 18
<212> TYPE: PRT
<213> ORGANISM: Bos sp.

<400> SEQUENCE: 24

Leu Ile Glu Glu Ala Ala Ser Arg Ile Val Asp Ala Val Ile Glu Gln
 1               5                  10                  15
Val Lys

<210> SEQ ID NO 25
<211> LENGTH: 18
<212> TYPE: PRT
<213> ORGANISM: Bos sp.

<400> SEQUENCE: 25

Leu Leu Ile Glu Thr Ala Ser Ser Leu Val Lys Asn Ala Ile Glu Leu
 1               5                  10                  15
Ser Val

<210> SEQ ID NO 26
<211> LENGTH: 18
<212> TYPE: PRT
<213> ORGANISM: Bos sp.

<400> SEQUENCE: 26

Leu Leu Ile Glu Thr Ala Ser Ser Leu Val Lys Asn Ala Ile Gln Leu
 1               5                  10                  15
Ser Ile

<210> SEQ ID NO 27
<211> LENGTH: 18
<212> TYPE: PRT
<213> ORGANISM: Bos sp.

<400> SEQUENCE: 27

Thr Pro Glu Glu Val Ala Ala Glu Val Leu Ala Glu Val Ile Thr Ala
 1               5                  10                  15
Ala Val

<210> SEQ ID NO 28
<211> LENGTH: 18
<212> TYPE: PRT
<213> ORGANISM: Bos sp.

<400> SEQUENCE: 28

Leu Glu Glu Lys Val Ala Ala Ala Leu Val Ser Gln Val Gln Leu Glu
 1               5                  10                  15
Ala Val

<210> SEQ ID NO 29
<211> LENGTH: 18
<212> TYPE: PRT
```

```
<213> ORGANISM: Bos sp.

<400> SEQUENCE: 29

Thr Val Glu Gln Tyr Ala Arg Lys Val Val Gly Asp Thr Leu Glu Leu
  1               5                  10                  15

Ser Leu

<210> SEQ ID NO 30
<211> LENGTH: 18
<212> TYPE: PRT
<213> ORGANISM: Bos sp.

<400> SEQUENCE: 30

Glu Leu Glu Thr Lys Ser Ser Lys Leu Val Gln Asn Ile Ile Gln Thr
  1               5                  10                  15

Ala Val

<210> SEQ ID NO 31
<211> LENGTH: 18
<212> TYPE: PRT
<213> ORGANISM: Bos frontalis

<400> SEQUENCE: 31

Pro Leu Glu Tyr Gln Ala Gly Leu Leu Val Gln Asn Ala Ile Gln Gln
  1               5                  10                  15

Ala Ile

<210> SEQ ID NO 32
<211> LENGTH: 18
<212> TYPE: PRT
<213> ORGANISM: Bos frontalis

<400> SEQUENCE: 32

Glu Leu Val Arg Leu Ser Lys Arg Leu Val Glu Asn Ala Val Leu Lys
  1               5                  10                  15

Ala Val

<210> SEQ ID NO 33
<211> LENGTH: 18
<212> TYPE: PRT
<213> ORGANISM: Bos sp.

<400> SEQUENCE: 33

Ser Gln Glu Gln Leu Ala Ala Glu Leu Ala Gly Tyr Thr Ala Lys Ile
  1               5                  10                  15

Ala Leu
```